(12) United States Patent
Milbocker

(10) Patent No.: US 6,540,659 B1
(45) Date of Patent: Apr. 1, 2003

(54) CARDIAC ASSISTANCE SYSTEMS HAVING BI-DIRECTIONAL PUMPING ELEMENTS

(75) Inventor: Michael T. Milbocker, Holliston, MA (US)

(73) Assignee: AbioMed, Inc., Danvers, MA (US)

( * ) Notice: Subject to any disclaimer, the term of this patent is extended or adjusted under 35 U.S.C. 154(b) by 0 days.

(21) Appl. No.: 09/723,628

(22) Filed: Nov. 28, 2000

(51) Int. Cl.[7] .................. A61N 1/365; A61N 1/362
(52) U.S. Cl. ..................... 600/17; 600/16; 623/3.21
(58) Field of Search ................ 600/16, 17; 623/3.21, 623/3.16

(56) References Cited

U.S. PATENT DOCUMENTS

| | | | |
|---|---|---|---|
| 2,826,193 A | 3/1958 | Vineberg | ............... 128/38 |
| 3,371,662 A | 3/1968 | Heid et al. | |
| 3,455,298 A | 7/1969 | Anstadt | |
| 3,464,322 A | 9/1969 | Pequignot | ............... 92/91 |
| 3,587,567 A | 6/1971 | Schiff | ............... 128/24.5 |
| 3,613,672 A | 10/1971 | Schiff | ............... 128/24.5 |
| 3,659,593 A | 5/1972 | Vail | |
| 3,674,019 A | 7/1972 | Grant | |
| 4,048,990 A | 9/1977 | Goetz | |
| 4,157,713 A | 6/1979 | Clarey | |
| 4,192,293 A | 3/1980 | Asrican | |
| 4,304,225 A | 12/1981 | Freeman | |
| 4,340,091 A | 7/1982 | Skelton et al. | |
| 4,411,268 A | 10/1983 | Cox | |
| 4,506,658 A | 3/1985 | Casile | |
| 4,536,893 A | 8/1985 | Parravicini | ............... 623/3 |
| 4,583,523 A | 4/1986 | Kleinke et al. | |
| 4,628,937 A | 12/1986 | Hess et al. | ............... 128/642 |

(List continued on next page.)

FOREIGN PATENT DOCUMENTS

| | | |
|---|---|---|
| EP | 0370931 | 5/1990 |
| EP | 583012 | 2/1994 |
| FR | 2645739 | 10/1990 |
| GB | 2115287 | 9/1983 |
| JP | 2271829 | 11/1990 |
| SU | 1009457 | 7/1983 |
| SU | 1734767 | 1/1992 |
| WO | WO94/21237 | 9/1994 |
| WO | 9922784 | 5/1999 |

OTHER PUBLICATIONS

Anstadt et al., *A New Instrument for Prolonged Mechanical Cardiac Massage (P)*, (Abstracts of the 38th Scientific Sessions); Supplement II to Circulation vol. XXXI and XXXII, II–43–44 (Oct. 1965).

Anstadt et al., *Direct Mechanical Ventricular Actuation: A Review*, Resuscitation, 21:7–23 (1991).

(List continued on next page.)

*Primary Examiner*—John Rivell
(74) *Attorney, Agent, or Firm*—Thomas J. Engellenner; Geoffrey S. Smith; Nutter McClennen & Fish LLP

(57) ABSTRACT

A unified, non-blood contacting, implantable heart assist system surrounds the natural heart and provides circumferential contraction in synchrony with the heart's natural contractions. The pumping unit is composed of adjacent tube pairs arranged along a bias with respect to the axis of the heart and bound in a non-distensible sheath forming a heart wrap. The tube pairs are tapered at both ends such that when they are juxtaposed and deflated they approximately follow the surface of the diastolic myocardium. Inflation of the tube pairs causes the wrap to follow the motion of the myocardial surface during systole. A muscle-driven or electromagnetically powered energy converter inflates the tubes using hydraulic fluid pressure. An implanted electronic controller detects electrical activity in the natural heart, synchronizes pumping activity with this signal, and measures and diagnoses system as well as physiological operating parameters for automated operation. A transcutaneous energy transmission and telemetry subsystem allows the Unified System to be controlled and powered externally.

20 Claims, 13 Drawing Sheets

U.S. PATENT DOCUMENTS

| | | | |
|---|---|---|---|
| 4,690,134 A | 9/1987 | Snyders | 128/64 |
| 4,731,076 A | 3/1988 | Noon et al. | |
| 4,803,744 A | 2/1989 | Peck et al. | |
| 4,813,952 A | 3/1989 | Khalafalla | |
| 4,827,932 A | 5/1989 | Ideker et al. | 128/419 D |
| 4,902,291 A | 2/1990 | Kolff | |
| 4,925,443 A | 5/1990 | Heilman et al. | |
| 4,936,857 A | 6/1990 | Kulik | 623/3 |
| 4,957,477 A | 9/1990 | Lundbäck | 600/16 |
| 5,078,134 A | 1/1992 | Heilman et al. | |
| 5,098,369 A | 3/1992 | Heilman et al. | 600/16 |
| 5,111,818 A | 5/1992 | Suzuki et al. | |
| 5,119,804 A | 6/1992 | Anstadt | 128/64 |
| 5,131,905 A | 7/1992 | Grooters | 600/16 |
| 5,169,381 A | 12/1992 | Snyders | |
| 5,243,723 A | 9/1993 | Cotner et al. | |
| 5,256,132 A | 10/1993 | Snyders | |
| 5,273,518 A | 12/1993 | Lee et al. | |
| 5,336,254 A | 8/1994 | Brennen | 607/129 |
| 5,344,385 A | 9/1994 | Buck et al. | |
| 5,348,528 A | 9/1994 | Vince | |
| 5,534,024 A | 7/1996 | Rogers et al. | 623/1 |
| 5,558,617 A | 9/1996 | Heilman et al. | |
| 5,564,142 A | 10/1996 | Liu | |
| 5,611,085 A | 3/1997 | Rasmussen | |
| 5,702,343 A | 12/1997 | Alferness | 600/37 |
| 5,704,891 A | 1/1998 | Mussivand | |
| 5,707,336 A | 1/1998 | Rubin | |
| 5,713,954 A | 2/1998 | Rosenberg et al. | 623/3 |
| 5,741,316 A | 4/1998 | Chen et al. | |
| 5,800,528 A | 9/1998 | Lederman et al. | 623/3 |
| 5,848,962 A | 12/1998 | Feindt et al. | |
| 5,853,005 A | 12/1998 | Scanlon | |
| 5,902,229 A * | 5/1999 | Tsitlik et al. | 600/16 |
| 5,971,910 A | 10/1999 | Tsitlik et al. | 600/16 |
| 5,991,665 A | 11/1999 | Wang et al. | |
| 5,991,925 A | 11/1999 | Wu | |
| 6,065,154 A | 5/2000 | Hulings et al. | |
| 6,076,013 A | 6/2000 | Brennan et al. | |
| 6,179,793 B1 | 1/2001 | Rothman et al. | |
| 6,179,800 B1 | 1/2001 | Torrens | |
| 6,200,260 B1 | 3/2001 | Bolling | |
| 6,212,430 B1 | 4/2001 | Kung | |
| 6,221,103 B1 | 4/2001 | Melvin | |
| 6,224,540 B1 | 5/2001 | Lederman et al. | |

OTHER PUBLICATIONS

Anstadt et al., *Pulsatile Reperfusion After Cardiac Arrest Improves NeuroLogic Outcome*, Ann. Surg., 214(4):478–490 (Oct. 1991).

Bencini et al., *The 'Pneumomassage' of the Heart*, Surgery, 39(3):375–384 (Mar. 1956).

Capouya et al., *Girdling Effect of Nonstimulated Cardiomyplasty on Left Ventricular Function*, Ann. Thorac. Surg., 56:867–871 (1993).

Carpentier et al., *Dynamic Cardiomyoplasty at Seven Years*, The Journal of Thoracic and Cardiovascular Surgery, 106(1):42–54 (Jul. 1993).

Carpentier et al., *Myocardial Substitution with a Stimulated Skeletal Muscle: First Successful Clinical Case*, The Lancet, p. 1267 (Jun. 1, 1985).

Chekanov, *Nonstimulated Cardiomyoplasty Wrap Attenuated the Degree of Left Ventricular Enlargement*, Ann. Thorac. Surg., 57:1684–1685 (1994).

Kass et al., *Reverse Remodeling from Cardiomyoplasty in Human Heart Failure*, Circulation, 91(9):2314–2318 (May 1, 1995).

Vaynblat et al., *Cardiac Binding in Experimental Heart Failure*, Circulation, Supplement I, 92(8):1–380 (Oct. 15, 1995).

Vaynblat et al., *Cardiac Binding in Experimental Heart Failure*, Ann. Thorac. Surg., 64:81–85 (1997).

Geddes et al., *Power Capability of Skeletal Muscle to Pump Blood*, Trans. ASAIO, 37:19–23 (1991).

Langer, Robert et al., *Tissue Engineering*, Science, 260:920–926 (May 14, 1993).

Freed, Lisa E. et al., *Biodegradable Polymer Scaffolds for Tissue Engineering*, Bio/Technology, 12:689–693 (Jul. 1994).

* cited by examiner

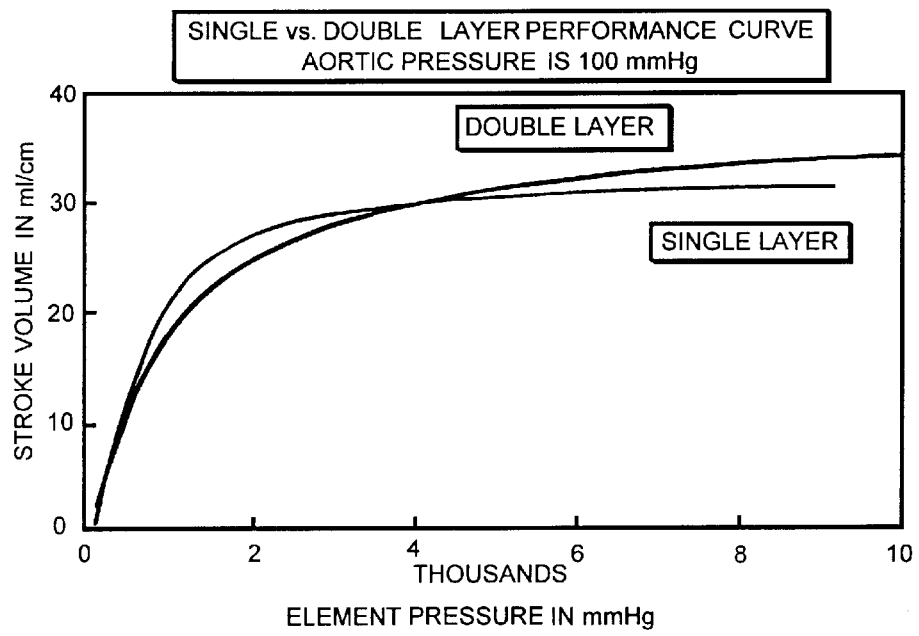
Figure 10
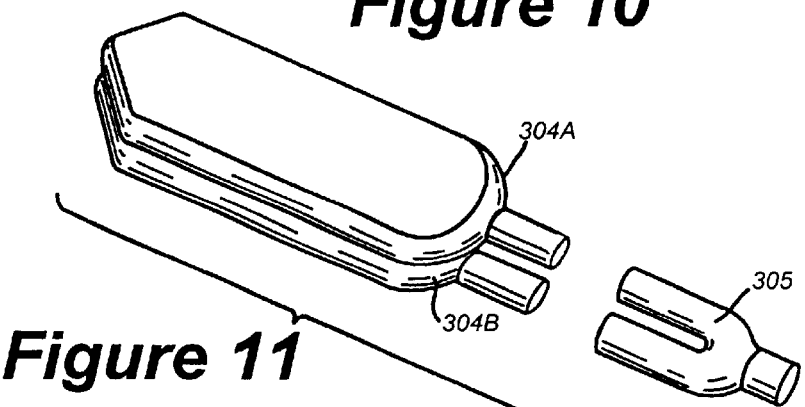
Figure 11
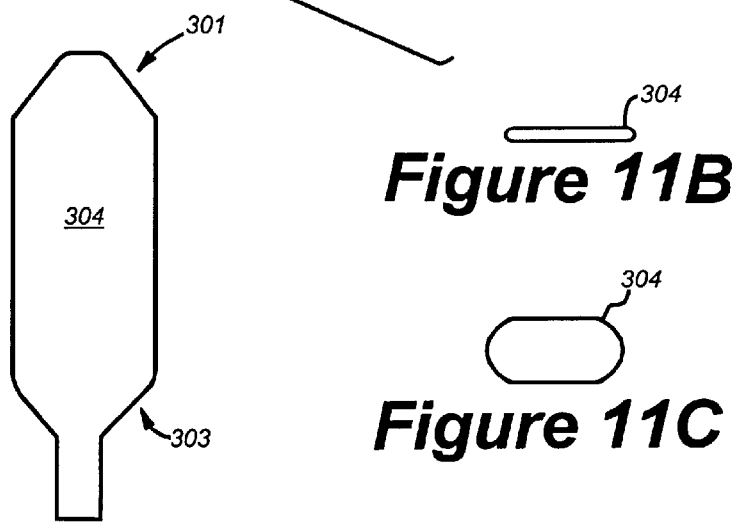
Figure 11A
Figure 11B
Figure 11C

CARDIAC ASSISTANCE SYSTEMS HAVING BI-DIRECTIONAL PUMPING ELEMENTS

GOVERNMENT FUNDING

The work described herein was supported, in part, by U.S. Government Grant Number NIH-NOI-HV-58154 awarded by the National Institutes of Health. The Government, therefore, may have certain rights in this invention.

BACKGROUND OF THE INVENTION

The present invention relates generally to cardiac assist and/or resuscitation systems for restoration or augmentation of natural blood flow and, more particularly, to implantable systems and associated methods for assisting the natural contractions of the heart.

Following a heart attack or as a result of other cardiac disease states, the heart's ability to pump blood can be seriously impaired. Conventional cardiac assist systems employ a variety of pumping approaches for assisting a failing natural heart. Generally, there are two categories of cardiac assist systems: those which contact blood, referred to herein as blood-contacting cardiac assist systems; and those which do not, referred to herein as non-blood-contacting cardiac assist systems.

A primary drawback of blood-contacting cardiac assist systems is the associated risk of thromboembolism. Although significant efforts have been made to reduce or eliminate this problem, the continued risk of thrombosis has restricted blood-contacting cardiac support systems to temporary or short-term applications. In addition to the risk of thrombosis, blood-contacting cardiac assist devices typically also experience calcification. The degree of calcification increases with time, again making these devices undesirable for long term applications.

Non-blood-contacting cardiac support systems significantly reduce the risk of thromboembolism and calcification. One conventional approach has been to directly apply forces to the heart so as to facilitate pumping. For example, U.S. Pat. No. 4,304,225 to Freeman discloses a non-contacting cardiac assist system designed to compress all or part of the heart by alternately tightening and releasing a circumferential compression band. Another conventional device, described in U.S. Pat. No. 4,583,523 to Kleinke et al., is an articulated mechanical device for applying an encircling force to the aorta. European Publication No. 0583012 A1 to Heilman et al. teaches the application of a similar device to the heart. Still other conventional systems, such as U.S. Pat. No. 4,411,268 to Cox and U.S. Pat. No. 4,813,952 to Khalafalla disclose an approach of encircling the heart with the latissimus dorsi muscle to achieve a desired compression of the heart.

Another class of non-blood-contacting cardiac assist devices uses hydraulic or gas pressure to displace an equivalent volume of blood in the heart through pressure applied to the outer surface of the heart, the epicardium. One conventional approach has been to use a housing of rigid construction for enveloping, at least partially, the ventricular region of the myocardium. The inner surface of the housing typically has a distensible elastic membrane adjacent to the myocardial wall. Pumping fluids are fed to the chambers defined by the housing and the membrane to apply pressure on the myocardial wall. In some instances the outer portion of the housing is formed of a flexible, non-distensible, member with an elastic distensible inner membrane. In general these conventional approaches utilize one or more compartments, each characterized by an elastic inner wall and an inelastic outer wall. Filling the compartments compresses the myocardium of the ventricle to aid pumping. When pumping is facilitated in this manner, a volume of inflating fluid or gas is required to displace an equal volume of blood. Cardiac assist devices of this general class are described in U.S. Pat. Nos. 2,826,193; 3,371,662; 3,455,298; 3,587,567; 3,613,672; 4,048,990; 4,192,293; 4,506,658; 4,536,893; 4,690,134; 4,731,076; 5,119,804; 5,131,905; 5,169,381; and 5,273,518.

Other approaches have employed a concave, gel-filled compression pad activated by a plate on its outer surface (U.S. Pat. Nos. 4,925,443; 5,098,369; 5,348,528); a cardiac assist envelope designed for minimally invasive implantation (U.S. Pat. No. 5,256,132); or a cardiac assist device having a fluid filled jacket encasing at least the heart ventricles to provide a compliant, completely passive support (U.S. Pat. No. 4,957,477).

A drawback to these cardiac assist devices is that they typically pump blood by displacing the blood with an equal inflation volume of a hydraulic fluid. As a result of this limitation, such systems require large reservoirs of the hydraulic fluid and/or complex pumping protocols.

To overcome this and other drawbacks, cardiac assist devices have been devised which displace blood with an inflation volume smaller than the displaced blood volume. Such cardiac assist devices typically produce higher pumping capacities through the injection of a relatively smaller quantity of fluid or gas under high pressure. Generally, these devices utilize a chamber or wrap having a number of inflatable segments.

For example, commonly owned U.S. Pat. No. 5,713,954 to Rosenberg et al. describes a non-blood-contacting cardiac assist device having tubes that contract a circumference of the heart when inflated. In one embodiment, the Rosenberg device is constructed of vertically-oriented, cylindrical (tube-shaped) inflation chambers arranged to form a ring and surrounded by a nondistensible sheath to form an artificial myocardium or heart wrap. The administration of a fluid under pressure causes the tubes of these conventional devices to have an expanded cross section, which is generally circular. When the fluid is withdrawn, the tubes flatten perpendicular to the direction of force generated by the pressure in the heart. When the tubes are deflated, the circumference of the pumping chamber is equivalent to the value of the number of tubes in the wrap multiplied by one half the circumference of one of the constituent tubes. When the tubes are fully inflated, the circumference of the pumping chamber is equivalent to the product of the number of tubes and the inflated diameter of one of the constituent tubes. When the wrap circumference is minimized there is no dilation of the tube circumference.

The resulting contraction of the circumference of the heart wrap is maximally 36%. This limit is due to the geometry of the device and is independent of the radius of the tubes chosen. Therefore, the volume of each tubes can be made small while maintaining a constant ejection volume. However, the work done is, in all cases, the same. The result is that smaller tubes require a higher pressure to attain a circular cross section. In general, for constant work preformed, the inflation pressure is inversely proportional to the inflation volume.

U.S. Pat. No. 3,464,322 to Pequigot also discloses an artificial blood pumping chamber that has walls which are formed from an arrangement of inflatable tubes. A drawback of the Pequigot device is that the inflation chamber tubes are free to dilate when inflated. The Rosenberg device overcomes the drawbacks of the Pequigot device since the circumference of the inflation chambers of the Rosenberg device cannot exceed the dimensions of the fabric pockets in which they are imbedded. Consequently, the pumping action resulting from a contraction of the Rosenberg heart wrap is not defeated by dilation of the radii of the inflation chambers. Therefore, the Rosenberg device is more likely to reach the theoretical maximum contraction of 36%. However, like the Pequigot device, the Rosenberg device cannot exceed this limiting maximum contraction ratio.

One drawback with the above blood pumping devices is that the actual extent of contraction, expressed as a percentage of the circumference of the deflated pumping chamber, is dependent upon the amount of non-contracting space between the tubes. However, in practice, it is very difficult to inflate a sheet of tubes, joined only at a tangent, without inducing high stress in the tubes or in an encircling sheath. Maintenance of the tubes in close proximity at high pressure necessitates some non-contracting space between the tubes. Furthermore, since the pumping chamber is meant to fit snugly to the heart, allocation must be made for fitting the pumping chamber to the heart in situ. Consequently, the tubes must be spaced apart for this purpose. As a result, the ejection volumes produced by the heart as a result of the spacing apart of the tubes in these conventional devices are significantly less than desired. This drawback occurs even if the inflated portion of the pumping chamber's circumference were to produce its theoretical maximum of 36% diametric contraction.

What is needed, therefore, is a non-blood contacting ventricular assist device that generates a contraction, which exceeds the theoretical limit of conventional contractile balloon wraps, and hence, generates a greater maximum stroke volume. The device should not encumber the natural function of the heart and, in the event of failure, the device should not interfere with the natural pumping action of the heart. The possibility of further injury to the heart and adjacent vessels should also be minimized by providing gentle and physiologically correct pumping action. The device should not damage adjacent tissue or traumatize adjacent organs by compression or excessive localized temperatures. The ventricular assist device should also be configurable to assist the left, right or both ventricles.

In addition to cardiac assist devices which actively assist the heart in pumping blood (so-called "active devices"), the present invention also pertains to another type of heart assist device known as a "passive constraint" or simply a "passive" device. Passive devices serve to prevent cardiac expansion beyond a predetermined volumetric limit in patients suffering from cardiac dilation, hypertrophy and related conditions. In the absence of such constraint, the weakened heart muscle will lose its ability to pump blood and, in many cases, result in damage to the patient's heart valves. In passive devices, the goal is not to augment or replace the natural heart's pumping action but rather to assist the heart by applying a constraining force during the heart's expansion (diastolic) phase.

Ideally, a passive device wrapped around the heart should mimic the natural resistance of the heart muscle itself to over-expansion. A healthy natural heart will exhibit a characteristic relationship between ventricular pressure and volume, such that small amounts of pressure will initially result in a desired expansion of the ventricular volume. During activity or exercise, the ventricles must also response to higher pressures to accommodate a greater volumetric expansion and, thereby, permit increased ventricular output. However, to achieve a desired ventricular output, especially during normal activity or exercise, the maximum ventricular end-diastole volume must still be constrained or else the ventricle, during contraction, will be unable to eject the necessary quantity of blood.

Unfortunately, conventional passive devices exhibit constraining forces that typically are not well matched to the natural physiology. Even when such passive wraps are constructed from elastic materials that respond to increases in pressure in accordance with Young's law, the performance of such devices degrades over time, largely due to the in-growth of epicardial and/or interstitial cells within and around the device. This in-growth prevents the elastic elements of the device from stretching.

Thus, what is also needed is a passive cardiac device that can better mimic the natural heart's response to increases in diastolic pressure and, in particular, devices that can continue to function and respond to such pressures despite in-growth of cells over time.

SUMMARY OF THE INVENTION

Methods and apparatus are disclosed for providing assistance to the ventricles of a natural heart. In one aspect of the invention, ventricular assist devices, capable of encircling at least a portion of the heart, are disclosed having multiple layers of inflatable elements. Such multi-layer devices induce contractions that overcome the limits of conventional contractile balloon wraps, and hence, generate a greater maximum stroke volume. Pumping modules incorporating multiple layers of inflatable elements are disclosed to wrap around, or attach to, one or both ventricles of a natural heart, or to any-other blood containing structure that enables natural circulation. The invention also encompasses a unified system that integrates the pumping modules of the present invention with other major components required for mechanical heart massage into one system that is completely implantable into the human thorax.

Thus, a unified system according to the present invention can be composed of a highly efficient pumping module (described in more detail below), one or more reservoirs of fluid and a control module. The control module can include an internal electronic controller for generating a suitably shaped pressure wave to be synchronized with the natural contraction of the heart, pumps, valves and/or regulators for delivering a pressurized fluid to the pumping module and a suitable power supply. In one embodiment, the power supply can include a transcutaneous energy-receiving device, and/or an implantable battery for storage of the received energy. The control module can further include a data transceiver.

The pumping module can also include conduits for distributing the pressurized fluid to the various inflatable elements of the pumping unit and attachment elements for attaching the pumping unit to the heart. The attachment mechanism can include direct attachment elements or tethering devices intended to prevent the wrap from slipping off the heart.

In accordance with another aspect of the invention, an easily attachable (and in at least some instances, a readily detachable) pumping unit is disclosed that is constructed of thin, collapsible, non-distensible, biocompatible material, which encases a multi-layer arrangement of inflatable elements. The inflatable elements can also be bound by a sheath that holds them in a defined geometry. For example, in one arrangement, the encircling sheath can bind sets of two or more inflatable elements in individual pockets, such that when the sheath is wrapped about a heart, the inflatable elements of each pocket will be stacked or juxtaposed along a radial line. The sheath also serves to join the sets of inflatable elements to each other along a line perpendicular to said radial line. This second dimension thus forms a circumferential restriction when placed around the heart.

The inflation elements can be tapered at one or both ends, and the resulting wrap curved in a plane, so that when joined end-to-end to form a continuous band, the wrap describes approximately the surface of a paraboloid of revolution. In this configuration, the surface of wrap that faces the epicardium of the heart presents a plurality of pockets each of which contain multiple layers of inflatable elements. The inflatable elements can be filled at time of implantation to conform the wrap to the heart. In one embodiment, particularly useful in active devices that are intended to assist the natural heart's pumping action, the inflatable elements are filled with a flexible, deformable substance that substantially maintains its volume when compressed.

Unified systems according to the invention can further include one or more electrodes for implantation on the heart or at a suitable adjacent site (e.g., on the heart assist device), to sense the heart's electrical signals and synchronize pump activation with the heart's cycle. For example, the sensor can detect and/or monitor well-known EKG components such as the p-wave, or the q-r-s-wave (indicating the beginning of systole) and/or the t-wave (at the end of systole). The signals from such sensor electrodes are then used by an electronic controller to synchronize the release of actuating fluid to the pumping unit and, subsequently, to synchronize the evacuation of fluid from the pumping unit.

The unified system can further include an energy converter (e.g., a pump) and at least one plenum for storage of a pressurized volume of fluid of sufficient size to provide a flow at nearly constant pressure during systole and to provide a flow away from the heart assist device at nearly constant vacuum (i.e., at a pressure less than ambient) during diastole.

Fluid control can be accomplished in at least two different ways. In one embodiment, a single plenum is used to store the inflation fluid and a bi-directional constant pressure pump is used to both inflate and evacuate the heart assist device. The pump can be a electromechanical energy converter or a device that induced the patient's own skeletal muscles to power a pump, or it can be a hybrid of both. Alternatively two uni-directional pumps can be used in tandem to fill and empty the inflatable elements of the heart assist device.

In a second embodiment, two plenums can be employed. One plenum is provided for storage of evacuated fluid and is preferably maintained at a sufficient state of evacuation so as to provide evacuating flow at a nearly constant pressure during the evacuation interval. A second plenum is provided for filling the inflatable elements of the heart assist device and is preferably maintained at a sufficient state of pressurization so as to fill the heart-pumping unit at a nearly constant pressure during systole. The unified system can further include a mechanical device or energy converter for continuously pumping fluid from the evacuated plenum to the pressurized plenum. The system can further include a controller or regulators to maintain the plenums at their respective pressurized states. In one embodiment, the energy converter, controller and plenums are contained in a single housing, the back of which has a convex surface curvature compatible with the internal abdominal cavity.

The system can further comprise a mechanical device or energy converter for continuously pumping fluid from the evacuated plenum to the low pressurize plenum and maintaining their respective pressurized states, and a second energy converter for continuously pumping fluid from the evacuated plenum to the high pressure plenum while maintaining their respective states. The two energy converters can pump substantially different flows, with the high pressure energy converter pumping a substantially lower flow. The system can further include a housing for containing the plenums and energy converters, the back of which can have a convex surface curvature compatible with the internal abdominal cavity.

Control systems in accordance with another aspect of the present invention can be electrically coupled to one or more electrodes that sense the heart's electrical activity, and can further comprise an electronic controller for synchronized release of actuating fluid to the pumping unit for subsequent synchronized evacuation of fluid from the pumping unit. The system can also include a plenum for storage of a non-pressurized volume of fluid of sufficient size to provide a flow at nearly constant pressure during the release interval, said plenum used for storage of fluid, a mechanical device or energy converter for periodically pumping fluid from the storage plenum to the pumping unit and thus attaining a pressurized state in the pumping unit, said energy converter pumping toward the pumping unit during systole and pumping from the pumping unit during diastole, and a housing for containing the plenums and energy converter, the back of which has a convex surface curvature compatible with the internal abdominal cavity.

In an alternative system according to the present invention, the unified control system can also include: an internal electronic controller for receiving both AC and DC supply voltages, an external communication channel data stream and generating an actuating signal for the release of pressurized fluid, communication channel data stream and internal battery recharging signals, an actuating means for converting said actuating signal into a periodic movement of the valve member(s), a pumping unit having an associated attachment means wherein the unit is attached directly to the heart or tethered to sites near the heart, said sites providing a restoring force directed from the apex to the base so as to counter the forces applied to the wrap by the heart, a volume displacement chamber containing the energy converter and plenums, a hermetic coupling means for connecting said controller to said energy converter, said communication channel data streams and internal battery recharging signal; a detecting means for generating said actuating signal in response to an electrically derived signal from the heart and/or measurement of flows, pressures, tensions related to the heart's ventricles for generating said actuating signal, and a housing the back of which has a surface curvature compatible with the abdominal cavity for containing said electronic controller, said actuating means, said blood pumping unit, said hermetic coupling means and said detecting means connected so as to form a unified system.

In accordance with another aspect of the present invention, the unified system can include a rechargeable internal battery for subcutaneous implantation to supply an internal DC supply voltage. The system can further include an external battery for providing a DC voltage to an external controller; with the external controller converting DC voltage received from the external battery and/or external power supply to AC voltage for transfer by a subcutaneous energy transformer to power the unified system and/or for recharging external the internal battery. The system can also include a computer interface for connecting said device to a computer for control and monitoring of the device; a display means for control status and alarm display; a transcutaneous energy transformer for transmitting said AC voltage across the skin; a transcutaneous information telemetry unit for bi-directional transmitting said communication channel data streams between said external controller and the implanted components of the system; as well as a connector for connecting said internal battery to said internal controller and an in-line connector for connecting said transcutaneous energy transformer to the internal battery.

In accordance with another aspect of the present invention, the unified system can include an implantable stimulator to supply an internal DC stimulus voltage and a rechargeable internal battery controlled by an internal controller for actuating a selected patient's skeletal muscle with the muscle forming a component of a mechanical pressurizing system. This system can be electrically actuated so as to maintain a desired steady-state hydraulic fluid pressure so that pressurized fluid can be held in reserve in a plenum for transfer to a pumping unit, said pumping unit powered by the pressurized fluid reserve, and said mechanical pressurizing system providing for a evacuated side, this side attached to a second plenum which actively draws fluid from the pumping unit during diastole.

In accordance with another aspect of the present invention, the rechargeable internal battery can be controlled by the internal controller for actuating a selected patient's skeletal muscle; with the muscle forming a component of a mechanical pressurizing and electrical energy generating system. This system can be actuated so as to maintain a desired steady-state hydraulic fluid pressure so that pressurized fluid can be held in reserve in a plenum for transfer to the pumping unit via an electrically generating element. The pumping unit can thus be powered by the pressurized fluid reserve, with this mechanical pressurizing system providing for a evacuated side, which can be attached to a second plenum that actively draws fluid from the pumping unit during diastole. The pressurized plenum can further be fitted with an electrically driven valve on the output side and the evacuated plenum fitted with an electrically actuated valve on the input side, and the valves can be powered by the internal battery and controlled by the internal controller. The system can further include an optional external computer interface for connecting said device to a computer for control and monitoring of the device; a display means for control status and alarm display; a transcutaneous information telemetry unit for bi-directional transmitting said communication channel data streams between said external controller and the unified system; a connector for connecting said internal battery to said internal controller and an in-line connector for connecting said telemetry to said internal controller.

The control systems of the present invention can be totally implantable and require no physical connections through the skin to the outside. The system can be powered by an implantable battery or directly by a transcutaneous energy transfer system. The battery can be recharged by the transcutaneous energy transfer system or by a muscle powered device. The device can be controlled and monitored remotely via a transcutaneous information telemetry or by said internal electronic controller.

In addition, the device of the present invention can be adapted to pneumatic as well as hydraulic activation, and alternative energy sources may be utilized such as a Stirling type engine, osmotic pressure vessel, muscle powered generator or a nuclear thermal source.

Anatomical fit to the heart and the maximum contraction length of the wrap are important factors in the clinical success of non-blood contacting, volume-amplified inflatable cardiac assist devices. In addition to the contraction limitations of the single layer geometry, prior art devices typically also exhibit poor anatomical compliance ('fit'). In the present invention a superior fit is achieved by providing a multiple layer geometry with a contraction length large enough to provide adequate non-contracting regions for attachment and gathering.

Furthermore, the inflation elements are shaped so as to minimize the size of the non-contracting regions. Attaching a pocket between the pumping unit and natural heart can make refined fit adjustments. This pocket can be filled with a hydrogel in situ. The gel can form a thin protective and close fitting layer between the pumping unit and natural heart. The gel can also be constrained entirely within the pocket or allowed to permeate the pocket so as to form a bond between the epicardium of the natural heart and the pumping unit.

In one preferred embodiment, the major components of the invention are integrated so that their individual functions are complementary. The specifications on these individual components are representative of a unified solution to the problems outlined above and may be unique to the arrangement disclosed. They reflect not only the actuation of a physiologically acceptable contraction of the heart resulting in enhance blood flow through the heart, but also relate to issues of maintenance, failure modes, reliability, energy economy, biological compatibility, and quality of life.

Heart assist devices are disclosed to provide an arrangement of inflation chambers or tubes that, when placed in juxtaposition (e.g., forming concentric layers of tubes), generate a contraction which is substantially greater than 36% of the uninflated length or circumference.

In another preferred embodiment, the inflation chambers can be oriented so that their axes are oriented along, but not necessarily parallel to the major (longitudinal or vertical) axis of the natural heart. By employing elongate tubes that are generally aligned with longitudinal axis of the heart, efficiency of pumping is further enhanced because the contractile dimension of the device is aligned with the natural (circumferentially inward) contractile direction of the heart.

The present invention also provides a method of positioning and layering the inflation chambers, and an arrangement of non-contracting regions (accounting for as much as 40% of the wrap's circumference) which allows for in situ fit adjustments while maintaining a contraction of at least 36% over the entire length of the wrap. The present invention further provides specifications for shape and dimension of the inflation chambers, and control of inflation that results in a gentle, effective, and physiologically correct contraction when the wrap is coupled to the heart.

In another aspect of the invention, improved designs and structures for heart-contacting assistance devices are disclosed. For example, the pumping modules can further include a thin, flexible liner between the heart and the inflation chambers to pad the heart. Preferably, the liner is filled with a substance, such as a hydrogel material, which changes the shape, and not substantially the volume, of the liner when compressed. This liner provides a customized fit to the natural heart.

In another aspect, the invention also provides a ventricular assist device system which can wrap around the natural heart and assist the natural heart in pumping without coming into contact with blood, and further provides a device that mimics the pumping action of the natural heart and is not directly coupled to the heart, so that in the event of failure, the device does not interfere with the natural pumping action of the heart.

The present invention also provides a ventricular assist device that occupies a volume that is less than the volume of the ejected blood. Likewise, methods are disclosed in which the function of the heart muscle is assisted by generating an encircling contraction around the heart which exceeds the theoretical limit of single layer balloon wraps, and hence, generates a greater maximum stroke volume.

The pumping devices of the present invention can be fixed with respect to the human heart, but not necessarily directly attached to it, and all of which is free to move with respect to other organs or bones. Moreover, the devices can be configured suitably for use as a right, left, or bi-ventricular assist devices.

The invention can further encompass ventricular assist systems with a portion of the control electronics implanted within the patient and the remainder of the control electronics provided on a small portable unit to be worn on a belt or other clothing or externally attached to the patient's skin.

In yet another aspect of the invention, multi-layered balloon wraps can be used in passive assistance devices to provide structures that restrain cardiac hypertrophy and mimic the natural resistance of the heart tissue to overexpansion. By choosing an appropriate inflation pressure for the balloon elements and then sealing them, the fluid pressure within the balloons can provide a resistance analogous to the Frank-Starling effect exhibited by cardiac tissue.

In such passive systems, if the heart continues to dilate, the balloons will flatten more to accommodate the enlargement but the pressure applied to the heart by the balloons will be greater. Moreover, unlike mesh-type passive girdles, which rely upon an open structure to accommodate the expansion and contraction of the heart, the multi-layer inflatable structures of present invention permit the use of solid wrap devices, which are less likely to loss their effectiveness over time due to tissue in-growth.

In addition, the passive devices of the present invention can be adjusted. For example, if the heart shrinks, the balloon elements can be periodically filled to a greater extent in order to tighten the wrap and the pressure applied by the partially inflated balloons will be less.

The invention can also provide architecture that can be adapted to many different geometrical configurations to meet the requirements of different actuating techniques within the overall constraints of the invention.

BRIEF DESCRIPTION OF THE DRAWINGS

FIG. 10 is graph of performance curves for the single and double layer wraps illustrating regimes of enhanced stroke volume as a function of pressure;

FIG. 11 is schematic perspective illustration of a pair of tube or balloon elements useful in the present invention;

FIG. 11A is a top view of a single balloon element of FIG. 11;

FIG. 11B is a cross-sectional view of a single balloon element of FIG. 11 prior to inflation;

FIG. 11C is a cross-sectional view of a single balloon element of FIG. 11 upon inflation;

DETAILED DESCRIPTION

Generally, a ventricular assist system should satisfy a multiplicity of requirements beyond the basic requirement of pumping blood. The intra-thoracic blood-pumping component of the system should not encumber the natural function of the heart, and preferably has a mean density comparable to that of the heart. Moreover, in the event of failure, the device should not interfere with the heart. Furthermore, the system life and integrity should be sufficient so as to avoid risk of sudden system failure. The formation of thrombus within the heart and adjacent vessels should be minimized by providing for gentle and physiologically correct pumping action. The device should not damage adjacent tissue or traumatize adjacent organs by compression or excessive localized temperatures. The system should be implantable, preferably without connections through the skin. The system can be supplied periodically with an energy source, in some cases that energy may be transmitted transcutaneously.

First, the geometry of a pumping unit according to the present invention is described, followed by a discussion of the fit of the invention around the human heart. An exemplary construction of the pumping unit is presented and then the various components of a unified system are discussed.

Geometry and Construction

Figure 1A:
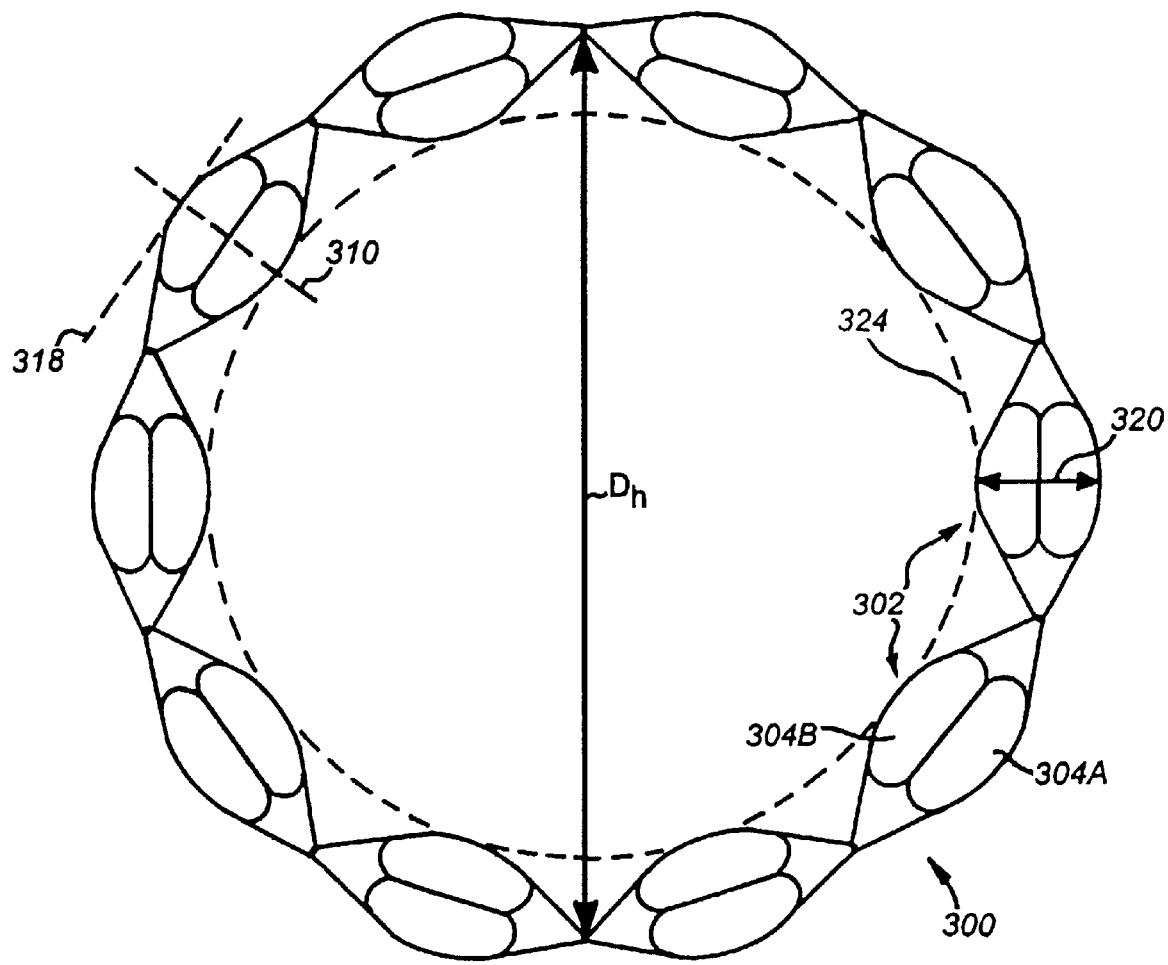
FIG. 1A is a cross-sectional view of a double layer wrap unit cell in accordance with one embodiment of the present invention.
Figure 1B:
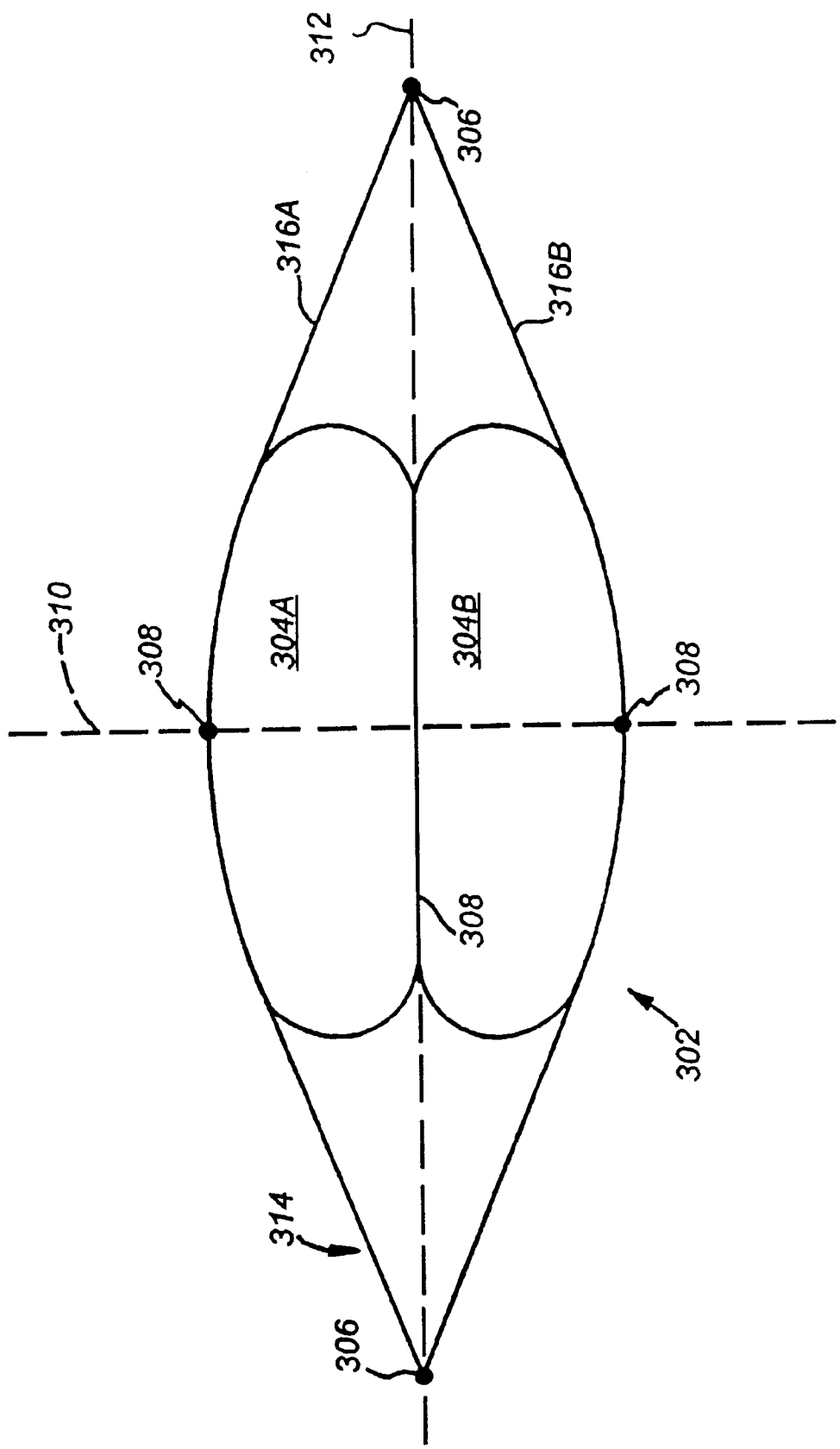
FIG. 1B is a cross-sectional view of a double layer wrap including the unit cells shown in FIG. 1A showing the geometric relationship of the partially inflated tubes and the encircled heart represented by a diameter of $D_h$.

FIG. 1A is a top-view of one embodiment of the multi-layer pumping chamber of the present invention illustrated in a partially-inflated state. Pumping chamber 300 includes a plurality of unit cells 302. FIG. 1B is a top view of one of the unit cells 302 shown in FIG. 1A. In the illustrative embodiment, each unit cell 302 includes two elongate inflatable chambers or tubes 304A and 304B (collectively and generally referred to as tubes 304). One skilled in the relevant art will appreciate that any number of tubes 304 can be utilized in the present invention. However, as will be described in detail below, in many applications, the two-tube structure 304 is a preferred embodiment because of the stability and simplicity that it provided.

Figure 2A:
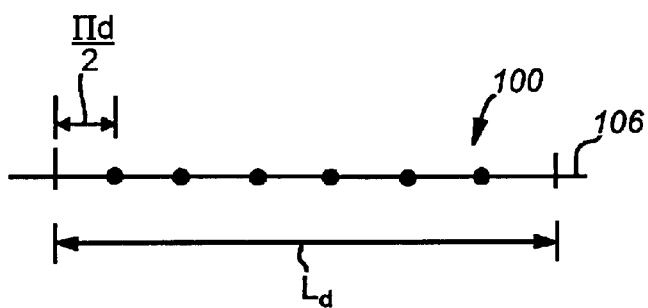
FIG. 2A is a cross-sectional view of a single layer wrap arranged in a plane shown in a relaxed (diastole) state.
Figure 2B:
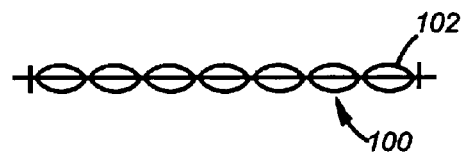
FIG. 2B is a cross-sectional view of a single layer wrap arranged in a plane shown in a partial contraction (mid-systole) state.
Figure 2C:
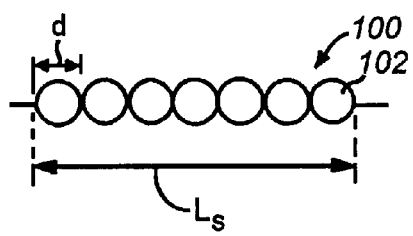
FIG. 2C is a cross-sectional view of a single layer wrap arranged in a plane shown in a full contraction (systole) state.

The benefits of the multi-layer pumping units of the present invention may best be described with reference to a conventional single layer pumping unit such as that described in commonly owned U.S. Pat. No. 5,713,954, herein incorporated by reference in its entirety. FIGS. 2A–2C are cross-sectional views of a conventional single layer pumping unit or wrap arranged in a plane and shown in three different states of contraction—a relaxed (diastole), partial contraction (mid-systole) and full contraction (systole) state. Together, these figures diagrammatically illustrate the operation of a conventional single layer pumping unit.

The single layer pumping unit 100 includes inflatable elements or tubes 102 juxtaposed in a plane 106 to form a flexible wrap. During diastole, the wrap 100 is under tension and not inflated. The cross-section of the individual tubes 102 is essentially flat as shown in FIG. 2A. The length of the wrap 100 attributable to each tube 102 is:

$$\frac{\pi d}{2},$$

and the length of the wrap 100 during diastole, $L_d$, may be expressed as shown in Equation (1):

$$L_d = n\frac{\pi d}{2} \tag{1}$$

where
 $L_d$=length of the pumping chamber 100 during diastole;
 n=number of tubes 102; and
 d=diameter of a fully inflated tube 102.

When the tubes 102 are fully inflated, as illustrated in FIG. 2C, the cross-section of each tube 102 is approximately circular. The length of the wrap 100 attributable to each tube 102 is essentially equal to the tube's diameter, d. Accordingly, the length of the wrap 102 corresponding to the systolic or contracted configuration, $L_s$, may be expressed as shown in Equation (2):

$$L_s = nd \tag{2}$$

where
 $L_s$=length of the pumping chamber 100 during systole;
 n=number of tubes 102; and
 d=diameter of a fully inflated tube 102.

Figure 3:
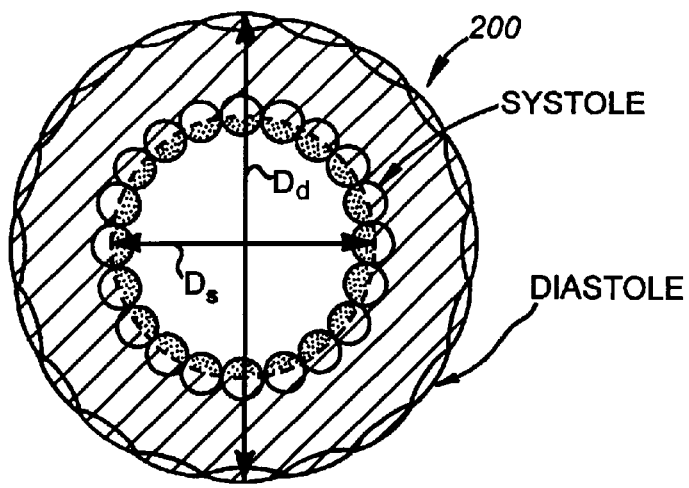
FIG. 3 is a cross-sectional view of a single layer wrap arranged in a cylinder showing the systolic and diastolic shapes of the heart muscle in a cylindrical geometry.

FIG. 3 is a cross-sectional view of a natural human heart and the conventional single layer pumping unit 100 illustrated in FIGS. 2A–2C, showing the cylindrical systolic and diastolic shapes of the pumping unit 100. As shown in FIG. 3, wrap 100 is joined end-to-end to form a continuous cylindrical shape. If the tubes 102 are collapsible but non-distensible, then d is the diameter of the circular cross-section of an individual tube at any non-negative pressure provided the wrap 100 is not in tension. When the wrap 100 is under tension, a minimum pressure is required for the tubes 102 to assume a circular cross section with a diameter d. When the tubes 102 are fully inflated, the diameter of the cylindrical wrap 100 corresponding to the systolic state, $D_s$, is approximated by Equation (3):

$$D_s = \frac{nd}{\pi} \tag{3}$$

where
 $D_s$=diameter of the cylindrical wrap 100 corresponding to the systolic state;
 n=number of tubes 102; and
 d=diameter of a fully inflated tube 102.

On the other hand, when the tubes 102 are no longer inflated and are collapsed, then the diameter of the cylinder 200 corresponding to the diastolic state, $D_d$, is approximated by Equation (4):

$$D_d = \frac{n\left(\frac{\pi d}{2}\right)}{\pi} \tag{4}$$

where
 $D_d$=diameter of the cylindrical wrap 100 corresponding to the diastolic state;
 n=number of tubes 102; and
 d=diameter of a fully inflated tube 102.

Since the circumference of a cylinder is linearly proportional to its diameter, the diameter of the cylindrical wrap 100 corresponding to both, the diastolic and systolic states, are reduced by the same percentage when the tubes 102 are inflated. The percentage of reduction in each is expressed in Equation (5):

$$\frac{D_d - D_s}{D_d} = 36\% \tag{5}$$

where
 $D_d$=diameter of the cylindrical wrap 100 corresponding to the diastolic state; and
 $D_s$=diameter of the cylindrical wrap 100 corresponding to the systolic state.

This is a limitation on the contractility of both wrap 100 and single layer wraps in general. This limitation is imposed by the geometry of the wrap 100 and is not affected by the number of tubes 102(n) or the diameter (d) of the tubes 102.

With reference again to FIG. 1B, the tubes 304 are wrapped in a non-distensible sheath 314. The tubes 304 are connected to the sheath 314 and to each other at a tangent along their axes, referred to herein as tangential connection regions 308. The sheath 314 includes two layers 316A and 316B on opposing sides of the tubes 304. The two layers 316 are connected to each other periodically along the length of the sheath 314 at cell connection regions 306. The tubes 304 are oriented within the enveloping sheath 314 to form a unit cell 302. A center line 312 resides in a plane that passes through the unit cell 302 and includes the cell connection regions 306. Assuming the tubes 304 contain substantially the same volume of fluid or gas, then the plane including the axis 312 also includes the tangential connection region 308 at which the two tubes 304 are connected. A second center line 310 shown in FIG. 1B passing through the center of the tubes 304 is substantially perpendicular to the centerline 312 through the center of the associated unit cell 300. When the pumping unit 300 is formed into a cylinder as shown in FIG. 1A, the center lines 310 of the tubes 304 are also substantially perpendicular to a tangent 318 on the cylinder 316.

The sheath 314 is preferably configured to fit snugly around the two tubes 304 when the tubes 304 are fully inflated. The mean circumference, $C_s$, of the sheath 314 for the exemplary 2-tube layer is approximated by Equation (6):

$$C_s = 2\pi r + 4r \tag{6}$$

where $C_s$=circumference of the sheath 314; and r is the fully inflated tube radius.

The width 320 (FIG. 1A) of the cell 302 is determined by the inflation of the tubes 304. Neglecting tube wall thickness, the collapsed width, $W_c$, of a cell 302 as measured along the axis 312 is given in Equation (7).

$$W_c = \frac{C_s}{2} \tag{7}$$

Since the width of the cell 302 is taken along the axis 312, the inflated width, $W_i$, of the cell 302 is given in Equation (8):

$$W_i = 2r \tag{8}$$

where
- $W_c$=the collapsed width of a cell 302 as measured along the axis 312;
- $W_i$=the inflated width of a cell 302 as measured along the axis 312; and
- r=the radius of a fully inflated tube 302.

For the exemplary 2-layer pumping chamber 300, the fractional length change of the unit cells 302 perpendicular to the tube axis 310 and horizontal axis 312, $F_d$, is given by Equation (9):

$$F_d = \frac{\frac{C_s}{2} - 2r}{\frac{C_s}{2}} = \frac{\pi}{\pi+2} = 61.1\% \tag{9}$$

where
- $F_d$=fractional length change of a 2-tube unit cells 302;
- $C_s$=circumference of the sheath 314; and
- r=radius of a fully inflated tube 302.

The fractional length change, $F_n$, of the circumference, $C_w$, of an n-layer wrap is given by Equation (10):

$$F_n = 1 - \frac{2}{\pi + 2(n-1)} \tag{10}$$

where
- $F_n$=fractional length change of an n-tube unit cell 302;
- n=the number of tubes in each unit cell.

Applying these relationships to alternative embodiments of the present invention with various number of tubes 304 yields a fractional length change of:

$F_1$=36.3%

$F_2$=61.1%

$F_3$=72.0%

$F_4$=78.1%

$F_5$=82.0% where $F_1$ is the conventional single layer geometry described above.

As shown, the greatest incremental difference in the fractional length, F, is between a single layer wrap geometry ($F_1$) to a double layer wrap geometry ($F_2$). However, significant increases in fraction length continues to occur as the number of tubes 304 in the unit cells 300 increases. When determining whether the double layer embodiment is to be used rather than the alternative embodiments which includes additional tubes 304, a tradeoff must be made between the utility of incremental gains in fractional length (F) achieved by the additional layers and the increased complexity required to prevent the additional tubes from buckling within the unit cells. (In certain embodiments of the invention wherein three or more tubes are included in each cell, supporting structures such as wires are used to secure the tubes 304 in a desired position to prevent such buckling).

The associated gains in stroke volume provided by the present invention can best be demonstrated on a comparative basis by considering a simplified geometry. If the heart is represented by a cylinder (shown by dashed line 324 in FIG. 1) wrapped by the pumping unit 300, then the stroke volume, $S_v$, is given by Equation (11):

$$S_v = \left(\frac{C_{wd}^2 - C_{ws}^2}{4\pi}\right)L \tag{11}$$

where
- $S_v$=stroke volume;
- L=length of the cylinder;
- $C_{wd}$=circumference of the cylinder in diastole; and
- $C_{ws}$=circumference of the cylinder in systole.

For any number (n) of tubes, the change in fractional length, $F_n$, of the wrap circumference, $C_w$, can be defined by equation 12:

$$\Delta F_n = \frac{C_{wd,n} - C_{ws,n}}{C_{wd,n}} \tag{12}$$

where
- $\Delta F_n$=change in fractional length ($F_n$) of the wrap circumference ($C_w$);
- n=number of tubes per unit cell;
- $C_{wd,n}$=circumference of the cylinder with n tubes per unit cell in diastole; and
- $C_{ws,n}$=circumference of the cylinder with n tubes per unit cell in systole.

Rearranging and solving for the circumference of the cylinder in systole yields the expression given in Equation (13):

$$C_{ws}^2 = (1-F)^2 C_{wd}^2 \tag{13}$$

where
- F=fractional length of an n-tube unit cell 302;
- $C_{wd}$=circumference of the cylinder with n tubes per unit cell in diastole; and $C_{ws}$=circumference of the cylinder with n tubes per unit cell in systole.

The stroke volume, $S_v$, follows as shown in Equation (14):

$$S_v = \left(1 - (1 - F^2)^2\right)\frac{C_{wd}^2 L}{4\pi} \qquad (14)$$

where $S_v$=stroke volume;
F=fractional length of an n-tube unit cell 302;
L=length of the cylinder; and
$C_{wd}$=circumference of the cylinder in diastole.

Letting $$L = 1 = \frac{C_{wd}^2 L}{4\pi},$$

the stroke volume for cells having n number of tubes is:

$S_{v,1}$=59.4%
$S_{v,2}$=84.9%
$S_{v,3}$=92.1%
$S_{v,4}$=95.2%
$S_{v,5}$=96.8%

The diastolic volume ($V_d$) of the heart or interior of pumping chamber or wrap 300 is given by Equation (15):

$$V_d = \frac{C_{wd}^2 L}{4\pi} \qquad (15)$$

where $V_d$=diastolic volume of the heart or interior of pumping chamber 300;
L=length of the cylinder; and
$C_{wd}$=circumference of the cylinder in diastole.

Conservation of energy provides a fixed relationship between work performed (W), stroke volume ($S_v$) at a given pressure (P) in the left ventricle, and device inflation volume ($V_H$) and hydraulic drive pressure ($P_H$). Energy conservation is given by the following well-known pressure-volume integral equation:

$$\int P_H dV_H = \int P dS_v = W \qquad (16)$$

Therefore, there is a tradeoff between changes in inflation volume and inflation pressure ($P_H$), the product of which is a constant.

Figure 4:
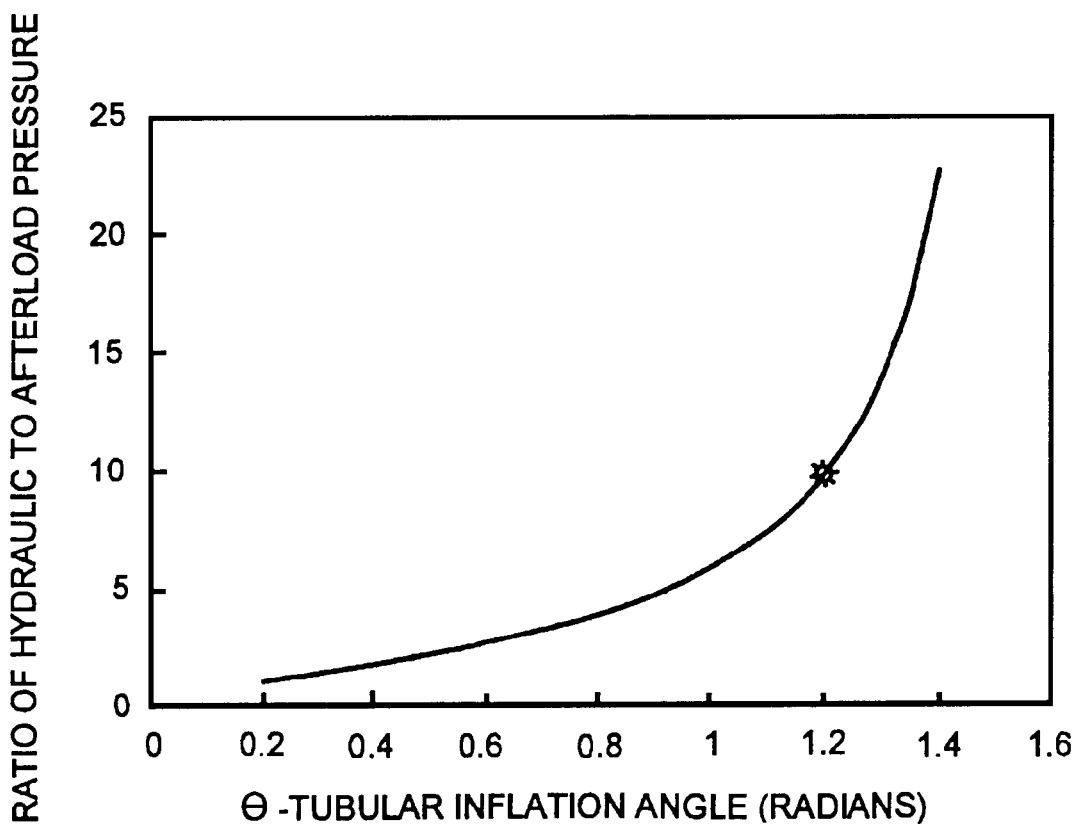
FIG. 4 is a graphical representation of the relationship between the hydraulic drive pressure to load pressure as a function of tube inflation.

FIG. 4 is a diagram illustrating a relationship between hydraulic drive pressure ($P_H$) and the load pressure as a function of selected tube inflation parameter, the tubular inflation angle (θ) introduced above. While the inflation pressure ($P_H$) rises steeply near full inflation (high inflation parameter), the change in inflation volume ($V_{tube}$) changes very little. Conversely, near deflation (low tubular inflation angle), inflation pressure ($P_H$) changes very little, but inflation volume, represented by tubular inflation angle θ, increases rapidly. These two characteristic behaviors are a consequence of the conservation of energy when a given pressure is applied to an inflatable tube, and is determined by the tube diameter (d). By decreasing the tube diameter (d), the inflation volume ($V_{tube}$) is decreased, which results in increased inflation pressures ($P_H$). As a result, the desired regime of inflation pressures ($P_H$) and inflation volumes ($V_{tube}$) can be tailored for any desired layer geometry by varying the tube diameter. It should be understood that the maximum attainable fractional contraction per unit length is constant due to the geometry of the unit cell 302.

In the present invention, the double layer design increases stroke volume significantly beyond limits attainable with a conventional single layer geometries. The double layer pumping unit 300 is sometimes preferred over embodiments of the present invention having more than two tubes due to the simplicity and inherent stability within the unit cell 302 when two tubes 304 are used. The double layer device therefore, in principle, offers enhanced design flexibility due to its greater maximum stroke volume. It can provide more pumping work per stroke than conventional single layer designs and is capable of being adjusted so as to either minimize inflation volume ($V_h$) or minimize the inflation pressure ($P_H$).

Figure 5:
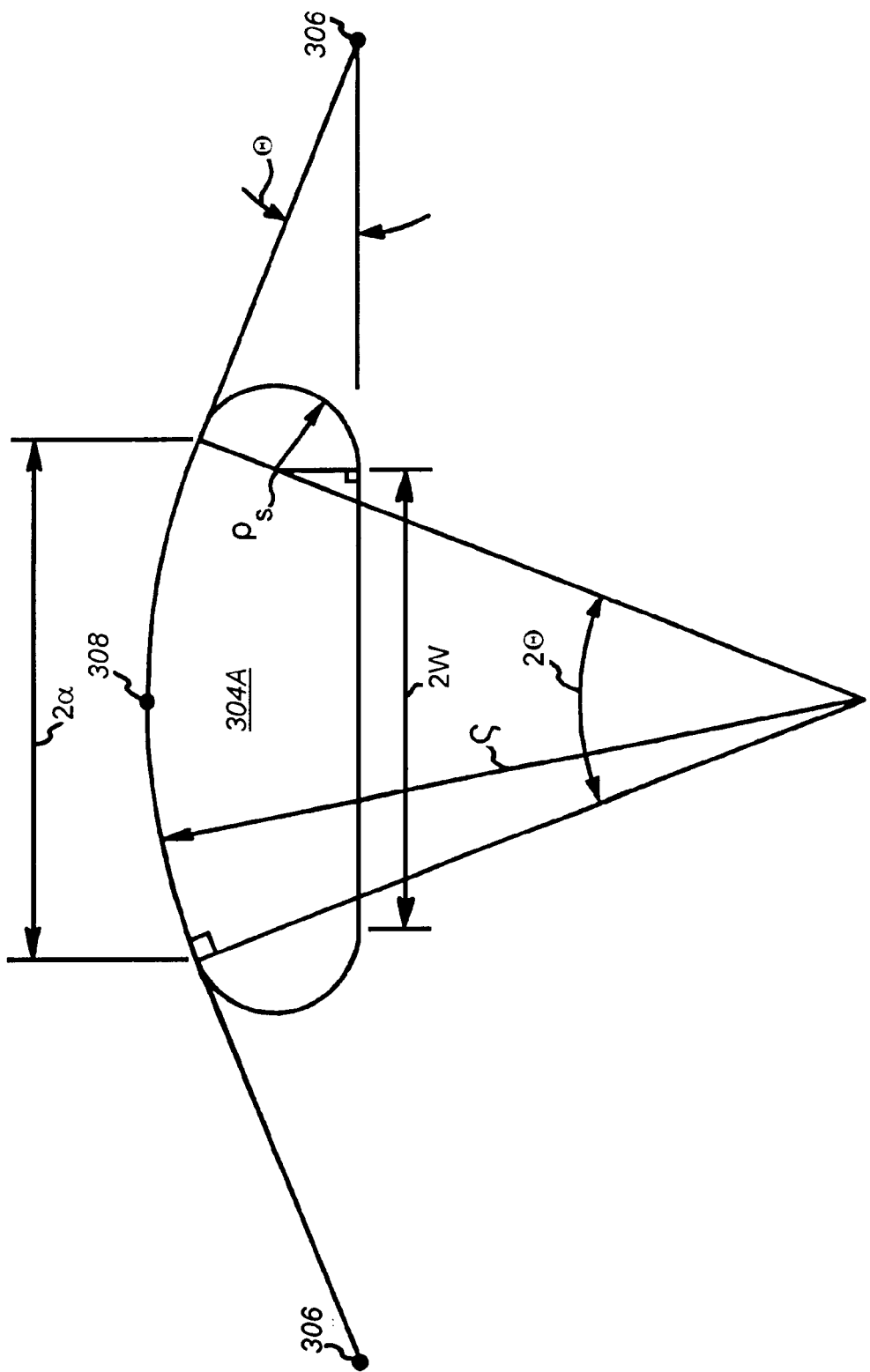
FIG. 5 is a schematic cross-sectional view of a partially inflated double layer device illustrating how unit cells are joined.
Figure 6:
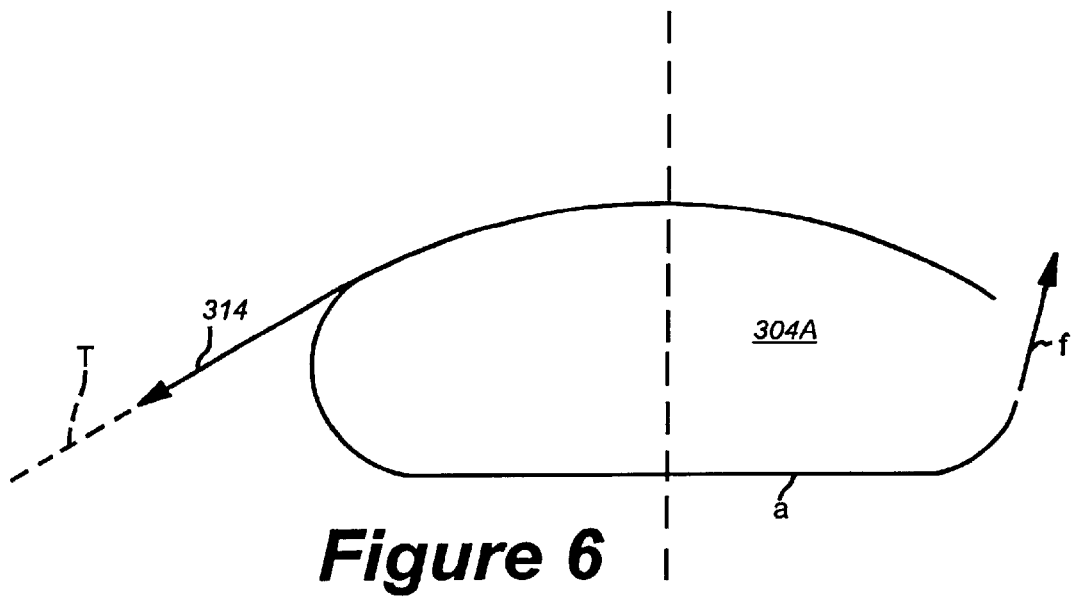
FIG. 6 is a further schematic representation of a double layer unit cell illustrating the forces acting on the cell during operation of the device.

Referring to FIGS. 5 and 6, the sheath 314 which forms the unit cell 300 in the double layer embodiment does not directly bear on the inflation pressure ($P_H$). In particular, at partial-inflation a portion of the tube circumference is in contact with the sheath causing the walls of the tube 304 and the sheath 314 bear the inflation pressure ($P_H$). Therefore, as shown in FIG. 5, forces at the cell connection points 306 of two unit cells 300 are directed along the sheath 314. In contrast, an analogous sheath in conventional single layer designs generates the greatest contraction when the sheath is in intimate contact with the tube at all stages of inflation. Decoupling the pressure bearing surfaces between unit cells offers important reliability and longevity advantages.

FIG. 6 shows a single unit cell 304 of the double layer device 300 in a partially inflated state. An analysis of the performance characteristics of the double layered wrap 300 is given below. The following assumptions were used to simplify the analysis:

1) All members are circular and connections between members are tangent. These assumptions are a direct consequence of Laplace's law.
2) There is no friction between the elements, all membrane are stressed and no folds exist.
3) The contact area between the elements is flat.
4) The number of elements is large such that the individual contraction ratio is equal to the total contraction ratio.

FIG. 6 is a schematic diagram illustrating the forces applied to one tube 304 of a unit cell 302. As shown in FIG. 6, there is symmetry of forces about a vertical axis. Thus, the following equations may be are derived from well-known force balance relationships for various free body diagrams within the individual unit cell 302. The vector sum of the tensions in the sheath 314 between adjacent unit cells 304 and the wall stress, T, must balance the force, f, generated by the ventricular pressure in contact with the area between the two tubes where they are joined. This yields the following relationship shown in Equation (17):

$$(T+f)\text{Sin}(\Theta) = P_H a \qquad (17)$$

where

T=tension in the connecting sheath between adjacent unit cells;
f=wall stress in the unit cell sheath;
$P_H$=hydraulic inflation pressure; and
a=contact area.

The vertical component of the tension (T) in the connecting sheath between adjacent unit cells 300 must balance the force (f) generated by the inflation pressure ($P_H$) as follows:

$$T \text{Sin}(\Theta) = P_H w \qquad (18)$$

where
  w=width of wrap or length of balloon;
  T=tension in the connecting sheath between adjacent unit cells; and
  $P_H$=hydraulic inflation pressure.

Figure 7:
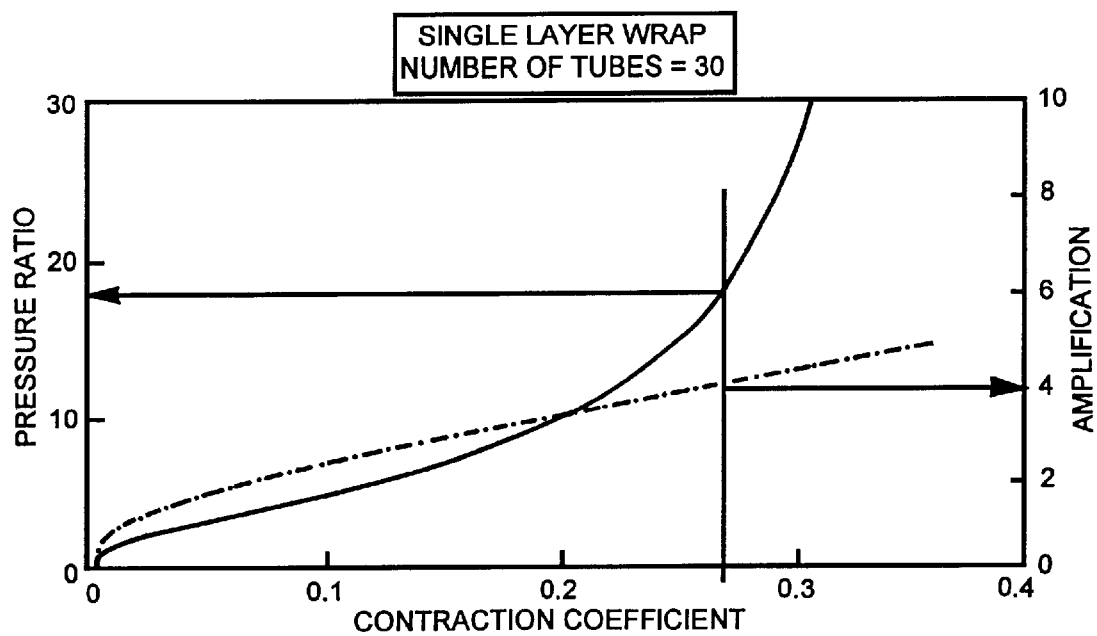
FIG. 7 is graph illustrating the relationship between pressure ratios, stroke volume amplification and contraction coefficient for a single layer wrap.
Figure 8:
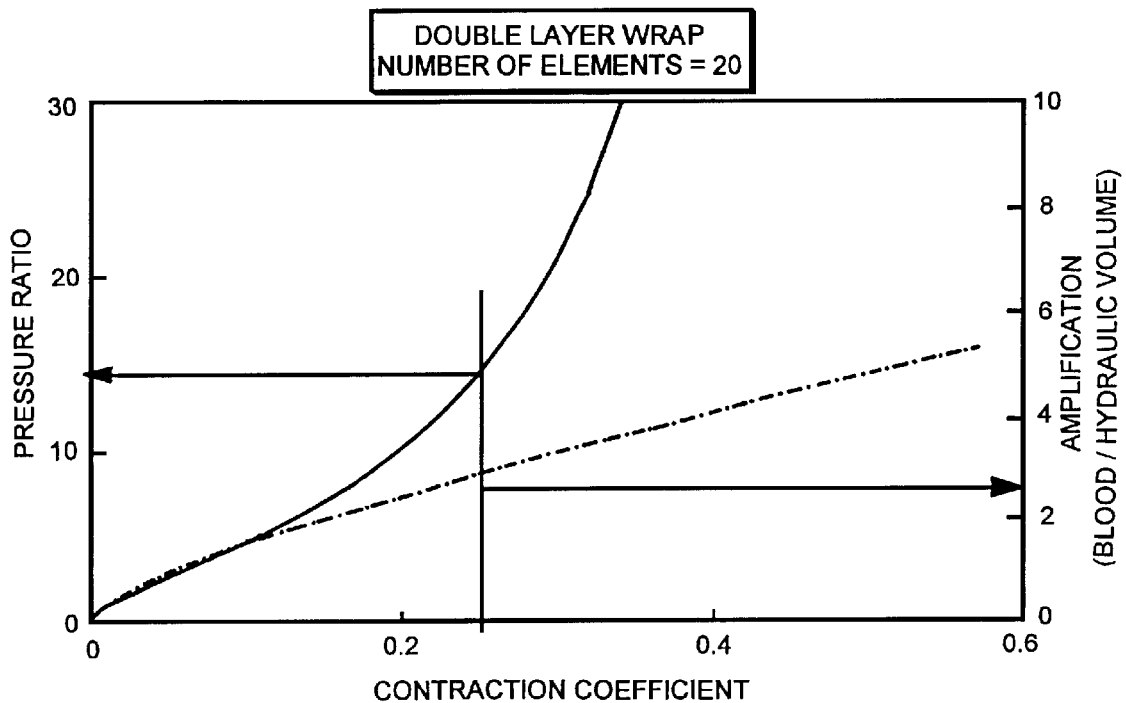
FIG. 8 is graph illustrating the relationship between pressure ratios, stroke volume amplification and contraction coefficient for a double layer wrap.

The theoretical performance of a conventional single wrap design and double layered pumping device according the present invention have been analyzed. FIGS. 7 and 8 are graphical representations of the hydraulic amplification and operating pressures as functions of device contraction. Device contraction is represented by a contraction coefficient. A contraction coefficient of 0 indicates no contraction. FIG. 7 (representing a conventional single layer arrangement) shows that a single wrap operating at an end systole pressure or maximum inflation pressure of 10 times the ventricular pressure($P_H$) (a pressure ratio of 10), will develop a hydraulic amplification of 3.5 when the contraction coefficient is 0.2 .

As shown in FIG. 8, a double layer device operating under similar conditions will generate a hydraulic amplification of 2.5. Hence, the fluid requirements of a conventional single layer device are lower than those of the double layer device of the present invention. Since the energy requirement is equal in both cases, the single layer device must operate at a higher average pressure to achieve the same end pressure.

Figure 9:
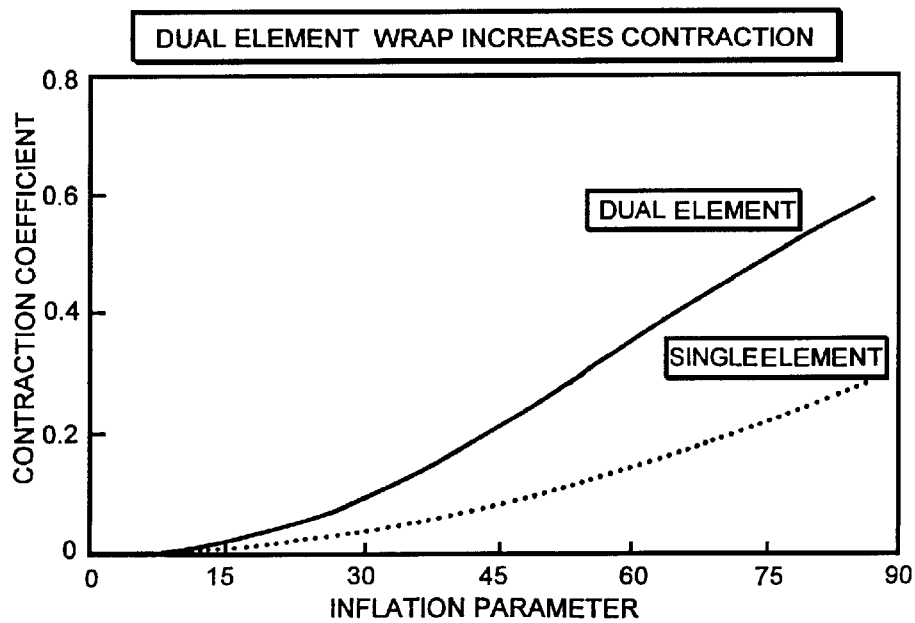
FIG. 9 is a graph of the contraction coefficient (1−F) as a function of fractional volumetric inflation for the single layer and the double layer wrap devices, showing that the single layer wrap converges to a contraction coefficient of 0.627 while the double layer wrap converges to 0.389.

FIG. 9 provides another illustration of the relationship between the contraction coefficient and a given inflation parameter for single and double layer wraps. Volumetric amplification $A_v$ is the ratio of the stroke volume of the heart $S_v$ divided by the change in balloon volume during a stroke. That is, $$A_v = \frac{S_v}{\Delta V_{balloon}} \tag{19}$$

FIG. 10 is an illustration of the relationship between the pressure applied to an individual tube element 304 and stroke volume for single and double layer wraps.

These graphic results illustrate two important features that differentiate the present invention from conventional single layer devices. In the case of a conventional single layer pumping unit, the ratio between stroke volume ($S_v$) and change in balloon volume is greater at every point during the contraction cycle than in the double layer device, regardless of the chosen contraction coefficient or inflation pressure. This is a direct consequence of the intrinsic differences between the PV curves of the two devices.

In the case of the double layer wrap 300, the maximum contraction coefficient is always larger than for the single layer wrap (see FIGS. 7 and 8). This characteristic is independent of the unit cell size. If an end contraction distance is specified, then the double wrap reaches this endpoint at a lower end inflation pressure for contraction coefficients less than 0.75.

In summary, the multiple-layer pumping chambers of the present invention have unique geometrical configurations that enable them to develop large contractions at low end inflation pressures.

In addition to the nondistensible sheath 304 in which unit cells 302 are formed to hold the elongate tubes 304, the pumping unit 300 can also include an inner pocket for in situ fit adjustment.

The sheath 314 can be composed of two layers of a woven, monofilament, polyester sheet material. For example, the filament size can be 30–100 microns, and the open area can be about 25% to about 50%. A pattern can be transferred to the fabric, and the pockets formed using either a tight sailing-type stitch or a polyester bonding technique. Alternatively, the sheath can be formed from a single urethane solution cast. The mandrel for casting a polymeric sheath can be a low melting point material or soluble polymer such as PEG, with through-holes that provide interconnections. The mandrel is dipped in a flocked urethane solution. The mandrel is removed by melting or dissolving. The resulting sheath is nondistensible yet flexible, and the pockets are delineated by the interconnects formed at the through-holes.

FIG. 11 is schematic perspective illustration of a pair of tube or balloon elements useful in the present invention. FIG. 11A is a top view of a single balloon element. Each of the balloon tubes 304A, 304B has a flatten cross-section, as shown in FIG. 11B prior to inflation and a cylindrical cross-section upon inflation as shown in FIG. 11C. The balloon tubes preferably have rounded ends 301 and 303. The balloon pairs can be made as a single unit or as two distinct balloons, as shown, and coupled to an inflation source via coupler 305. The balloons are preferably made of polyetherurethane. Mandrels of the desired shape are dipped to form balloons either as a pair or as singles. The desirable wall thickness being uniform and in the range of about 2 to about 10 mil.

Heart Fit

Figure 12:
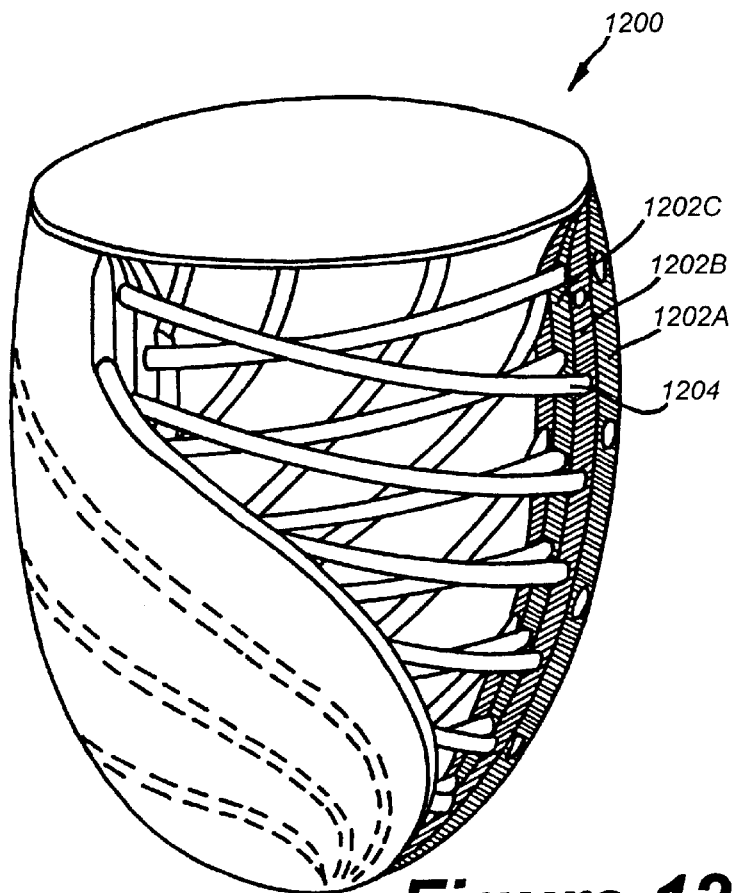
FIG. 12 is an illustration of the human heart showing the nested sets of fiber shells and the spiral path of the fibers in each shell.
Figure 13:
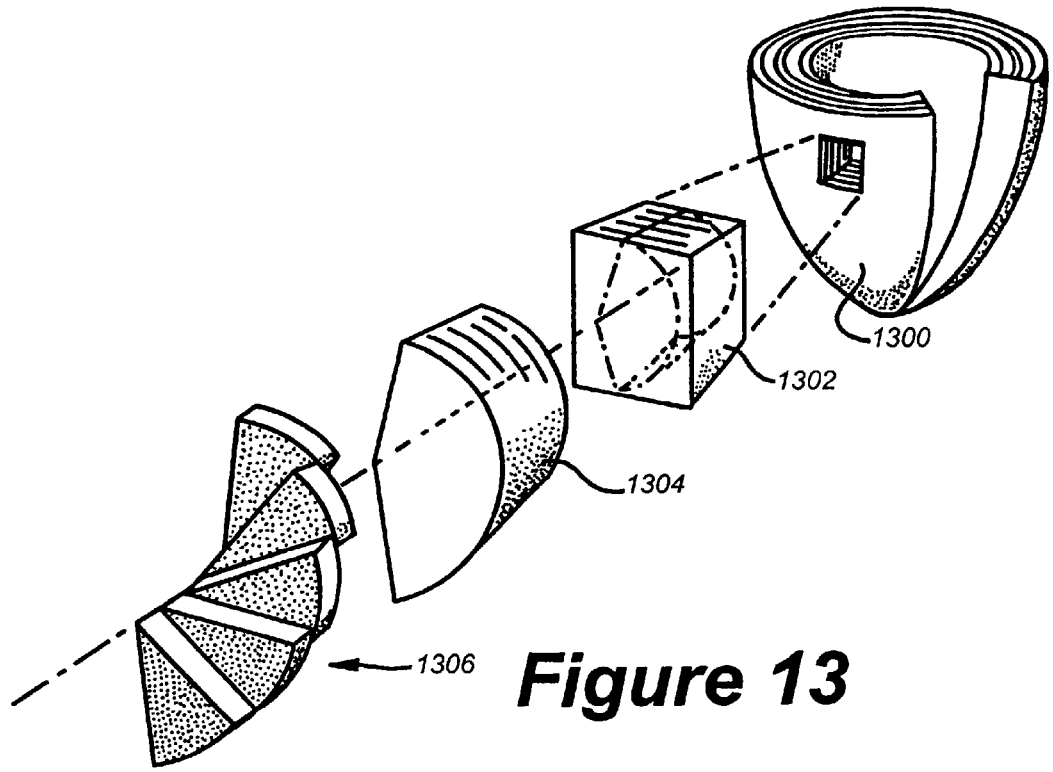
FIG. 13 is a schematic illustration of a section of cardiac muscle tissue.
Figure 14:
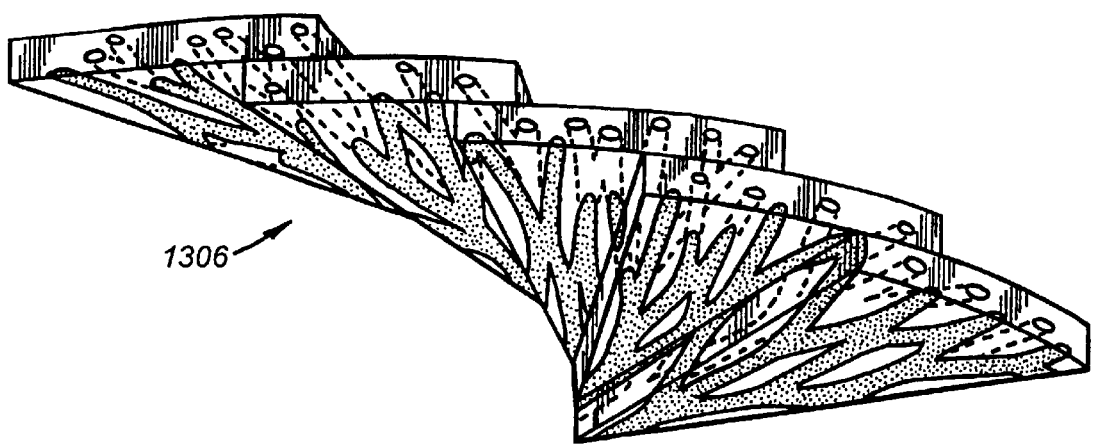
FIG. 14 is a further schematic illustration of the varying orientation of cardiac muscle fibers.

The manner in which the pumping unit 300 is secured or fit to a human heart is now described. FIG. 12 is a partial cut-away view of the human heart showing nested sets of fiber shells with each such shell having a spiral path of fibers. The shape of the heart is defined by the epicardium following a geodesic contour of a surface such that there is minimum surface; in particular, this shape is commonly referred to as a paraboloid of revolution. As shown in FIGS. 12–14, the myocardium can be visualized as a nested set of fiber shells. These figures have been derived from those provided in D D Streeter, C Ramon, "Muscle Pathway Geometry in the Heart Wall," IEEE Journal of Biomechanical Engineering, 105:367–371 (1983); D D Streeter, W T Hanna, "Engineering Mechanics for Successive States in Canine Left Ventricular Myocardium," Circ. Research, 33:656–664 (1973); D D Streeter, R N Vaishnav, D J Patel, H M Spotnitz, J Ross, E H Sonnenblick, "Stress Distribution in the Canine Left Ventricle During Diastole and Systole," Biomedical Journal, 10:345–363 (1970); and M A Ross, D D Streeter, "Nonuniform Subendocardial Fiber Orientation in the Normal Macaque Left Ventricle," European Journal of Cardiology, 3(3):229–247 (1975), all of which describe this construction of the human heart and which are hereby incorporated by reference in their entirety.

On each of the shells 1202 the muscle fiber 1204 travels in a spiral. Adjacent fibers 1204 in the same shell 1202 are substantially parallel as shown in FIG. 12. Proceeding from shell-to-shell, the angle of the fibers 1204 changes gradually. That is, the fibers 1204 in one shell 1202 are not parallel with the fibers 1204 in an adjacent shell 1202; instead, they are offset from each other by a few degrees.

Referring to FIGS. 13 and 14, the relationship between the shells 1202 of the heart are now described. A block 1302, 1304 removed from the full width of the wall 1300 of the heart 1202 reveals that the fiber orientation resembles that of the open blades of a Japanese fan, as shown by reference numeral 1306. On each shell 1202A, 1202B, etc., represented by a blade of the fan, the fibers follow the line of the blade, but each fiber is randomly tethered to its neighbor within the blade and from blade to blade. The fibers are restricted to a lateral sliding or rolling motion, and no fiber acts independently. Generally speaking, left ventricular fiber angles (in diastole and systole) can be seen as a function of percent wall thickness. The mean fiber angle (spatial orientation) changes continuously from about +60 degrees on the -endocardium surface to about −60 degrees on the epicardium surface.

Generally speaking, a two dimensional sheet structure can be bent into a paraboloid of revolution if V-shaped sections are periodically excised from the sheet, and adjacent edges thus formed are joined. However, if the V-shaped sections lie on a line, the resulting structure will be a cone. A cone can be distinguished from a parabola in that the edge of the parabola has an increasing slope. If the V-shaped sections are cut on two arcs such that when joined together along with the wrap ends, a shape which has a small slope on the apex side and a large slope of the base side is formed. The curvatures of the arcs are such that the arc forming the apex side has a shorter length than the one forming the base side is formed. Although the V-shaped sections forming the apex and the base are paired in one-to-one correspondence, the distance between adjacent V-shapes on the apical side is shorter than that on the base side. Based on these geometric principles, a pumping unit can be constructed in this way such that it develops a circumferential contraction around the heart when the tubes are oriented with their axis running from apex to base. Accordingly, the tubes can be located between apical-base paired V-sections. An enclosing sheath can be constructed from two such sheets, where pockets are formed by bonding or stitching the sheets together to form pockets. The outlines of the pockets would follow the contours of the V-shaped sections. Preferably, these pockets are slanted with respect to the axis of the heart so that they effect a contraction that is approximately 30–60 degrees from the midline.

Thus, the tubes (e.g., inflatable balloons) can be mounted in the pockets, such that the open end of the balloon extends out the apical or, alternatively the base side of the pumping unit. The portion of the balloon that is exposed is preferably fitted with a device for connection to a distribution network. The balloons are preferably tapered at both ends such that when they are inflated, a fabric sheath can be brought tightly against the balloon pair at all points. This "wrap," when placed around the heart, affects ejection of blood by reducing the circumference of the heart by direct volume displacement due to distention of the balloons toward the heart, and by a pressing action. In one preferred embodiment, the balloons can transform from a parabolic curvature induced by the diastolic heart to a straight tube configuration as a consequence of inflation and thereby eject greater volumes of blood.

In some applications it may be preferred that both ends of the balloon be closed. In such an embodiment, the connection point to the fluid source can be located between the ends and directed away from the heart so that any connecting tubing does not interfere with circumferential contraction. However, in tubes that are tapered at both ends, the weakest point of attachment is midway between the ends. The stresses can be defined as follows:
This choice is a consequence of considering the stresses at point r, σ(r), in the free balloon wall:

$$\sigma(r) = \frac{pr}{t} \tag{20}$$

where:
p is the pressure inside the balloon;
r is the radius of the balloon; and
t is the thickness of the balloon wall.
Consequently the highest local stresses are at points of largest radius of curvature. For this reason, a preferred embodiment entails tapered balloons with one end closed with a hemisphere, the hemisphere radius being half the balloon diameter at the point where the hemisphere joins the taper.

Considering the unit cell 300 described above comprising the two balloons 304A and 304B and the sheath 302. The inflated length of the sheath—$l_i$—may be represented by the expression given by:

$$l_i = l_o + \frac{d}{2} \tag{21}$$

where:
$l_i$ is the inflated length of the sheath;
$l_o$ is the part of the sheath corresponding to the straight part of the balloons 304; and
d is the inflated diameter of the balloon.
The flattened or deflated length of the sheath, $l_d$, is given by:

$$l_d = l_o + \frac{(\frac{\pi}{2} + 1)d}{2} \tag{22}$$

The shrink ratio, R, defined as the change in linear dimensions relative to the original linear $$R = \frac{\left[\frac{l_o + (\pi + 1)d}{2}\right] - \left[l_o + \frac{d}{2}\right]}{\frac{l_o + (\frac{\pi}{2} + 1)d}{2}} = \frac{\pi}{\frac{4l_o}{d} + \pi + 2} \tag{23}$$

dimension $l_d$ is:
The shrinkage, R, is a function of the ratio between the diameter d and the length $l_o$. This ratio is valid for any number of unit cells juxtaposed provided $l_o/d$ is identical for all such unit cells.

In one preferred embodiment, to achieve a desired fit, the wrap 300 is configured so as to shrink in proportion to the natural apical contraction of the heart. Typically, this is approximately 12%. Letting R=0.12 yields a length to diameter ratio of $l_o/d$=5.26. The diameter used here is the diameter where the balloon merges to form a hemisphere.

This does not take into consideration the taper in the balloon 304. There are a variety of tapers which are possible. All tapers involve a continuous transformation from a maximum diameter to a minimum diameter. The exact mathematical formula used to determine this profile will affect R as expressed below:

$$R = \frac{\left[\frac{l_o + (\frac{\pi}{2} + 1)d\lambda}{2}\right] - \left[l_o + \frac{d}{2}\right]}{\frac{l_o + (\frac{\pi}{2} + 1)d\lambda}{2}} \tag{24}$$

where the large diameter is D=dλ. The taper then is expressed by λ. In the particular case where D=10 mm, R=0.12, and $l_o$=80 mm, the value for lambda is λ=2.92. This value for lambda is compatible with the requirement that the taper provide a good fit to the heart when the balloon is deflated. It should be noted that to attain a 12% longitudinal contraction in the single layer design with tubes of the same diameter, two wraps would be required to cover the heart (as indicated in Ser. No. 08/490,080). In this event, a tapered design employing two wraps would impede ventricular filling at the junction of the two wraps.

Although a parabolic profile is a good fit to a side projection of the heart onto a plane, there are numerous variations in the longitudinal direction which translate into various distances from the heart's axis when measured on a line traveling in the circumferential direction on the epicardium. When the wrap performs a pumping action on a deformable "corrugated" surface such as that of the heart, the corrugated regions are filled by extension of the balloons and contraction of the wrap when inflated. This represents lost stroke volume, and studies on casts of dog hearts reveals this loss to be approximately 100% of the realized stroke volume.

The preferred embodiment contains a segmented or single pocket which extends over the entire surface of the wrap on the side facing the heart. This layer is preferably be filled with a compliant material which satisfies the following criteria:

1. have approximately the specific gravity of water
2. have the viscosity of water when first introduced into the wrap so that an in situ fit can be made
3. have the properties of a solid after a fit is made, such that the material does not pool to the apex and inhibit the proper filling of the heart
4. remain unchanged in a wet, 37° C. environment
5. be easily deformable but not change appreciably its volume
6. be nontoxic and biocompatible
7. does not release a gas, or is excessively exothermic or endothermic when transforming from a liquid state to a solid state
8. possess a low durometer reading so that it does not excessively load the wrap
9. possess an elastic quality which will aid in ventricular filling, and not impede ventricular filling in the event of system failure
10. have a slow setting time relative to the beat frequency of the heart so that an average heart shape results These requirements are satisfied by a number of generally available hydrogels. One example of a hydrogel which may be used in conjunction with the present invention is Hypol™ PreMA G series manufactured by Hampshire Chemical Corp., Lexington, Mass. Hypol forms a polyurethane matrix hydrogen bonded to up to 95% water by weight. The formation of a hydrogel layer between the wrap and the heart is an important aspect of the present invention. One embodiment provides for two entrance ports and an exit port affixed to the pocket. Preferably, the port is detachable and the entrance ports are positioned at opposite ends of the wrap with the exit port at a location midway between the two exit ports.

In one embodiment, a mixture of 10% Hypol and 90% water is mixed in a sealed blender type apparatus, or alternatively a mixing syringe. The ingredients mixable by breaking a separating membrane. The resultant mixed solution introduced to the wrap through entrance ports. The pocket is filled until fluid is detected at the exit port, and subsequently the exit port is sealed and the pocket gently pressurized so as to completely fill all voids between the wrap and the beating heart. The solution sets in 60 seconds, allowing for the liquid state of the pocket to be in contact with the beating heart for approximately 30 seconds. The solution sets in a continuous fashion, reaching a maximum durometer reading in about 10 seconds after setting begins. The setting time allows for the pocket to be modified by changes in the hearts shape through at least 10 heart cycles, so that the final shape is a fit to the mean heart shape. This provides for the least loading on the wrap.

Figure 15:
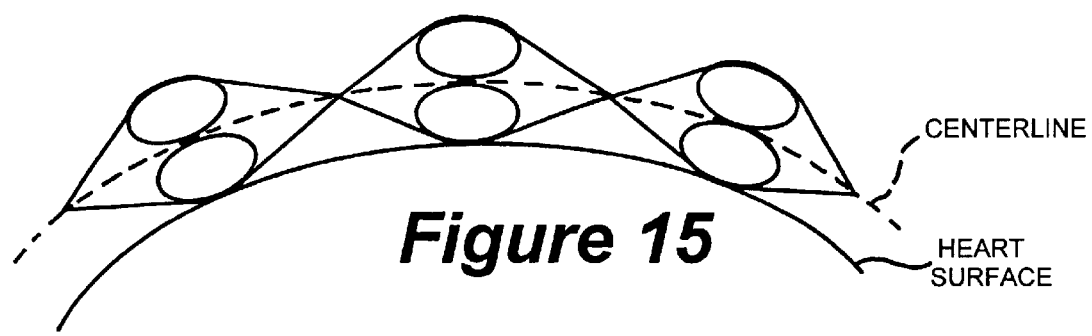
FIG. 15 is a partial cross-sectional view of a multi-layer cardiac wrap according to the invention.

Although both the single and double layer designs generate a radially pressing action, the following analysis shows that the pressing action is negligible for the single layer design. This action should be viewed as distinct from a direct volume displacement, which also occurs, and is caused when inflation of the balloons creates gaps between them. Referring now to, FIG. 15, the dashed line, or centerline, defines the locus of points which contract under inflation of the balloons. An inscribed line defines the surface of the heart. In the single layer design the gap is small enough for the heart or hydrogel to conform to the gently corrugated surface. In the double layer design the gap is deeper. Assuming now the heart does not conform to the device surface, but instead lies on the inscribed line, it is possible to calculate a hydraulic gain factor specific to the gap forming phenomenon. In this calculation only the inflation volume between the centerline and the natural heart is considered. For the single layer design the inflation volume per unit cell is one half the volume of a single balloon, and for the double layer it is one balloon volume. For the sake of comparison one can assume a spacing between adjacent balloons in the single layer design of 1 inch. The spacing between adjacent balloons in the double layer design can be 1.5 inches. Assume an inflation pressure of 30 psi. At this pressure the single layer design develops a maximum contraction of 34%, whereas in the double layer design it is only 40%. Recall that the theoretical maximum at any pressure for the single layer is 36%, whereas in the double layer design it is 61%.

The gap formed has a cross section defined by:

$$A = S \times C \times h \quad (25)$$

where:

S is the spacing;

C is the contraction; and h the displaced distance from centerline.

The displaced distance from the centerline, h, can be approximated by assuming $$(cx)^2 + h^2 = H^2 \quad (26)$$

where:

x is equivalent to S/2, and the hypotenuse H is S/2. Then $$h_{sigle} = \sqrt{(1-C^{2k})} = 0.37S \quad (27)$$

and $h_{sigle} = 0.4oS$.

The gap areas for a large balloon is 0.24 (2.2) for a single layer, and 0.54 (2.5) for a double layer. The portion of the gap filled by the cross section of the balloon is 0.11 for the single layer device and 0.22 for the double layer device. The gain factors are given in parentheses above. It is important to note that if the double layer were fully inflated to 59% contraction of a possible 61%, the gain factor is considerable larger for the double layer design: 0.84 (3.8).

Attachment

The pumping unit of the present invention may be attached to the heart. There are a variety of attachment approaches that are discussed in the literature. These approaches can be grouped into 6 categories: 1) direct suture of the wrap to the heart such as that described in U.S. Pat. No. 5,098,369; 2) those that use a strap through the transverse sinus or major vessels which are attached to the wrap, such as those described in U.S. Pat. Nos. 5,131,905 and 4,536,893; 3) those that utilize various chest cavity attachments, including attachment to the sternum or the rib cage, such as those described in European Patent No. 0 583 012 A1 and U.S. Pat. No. 4,925,443; (4) vacuum between the wrap and the heart, such as described in U.S. Pat. No. 5,119,804; (5) those that use a staple to attach the wrap to a surrounding tissue such as the pericardium, described on U.S. Pat. No. 4,690,134, or the diaphragm and (6) the use of mechanical griping elements on the inside of the wrap as described in commonly owned, co-pending U.S. patent application Ser. No. 09/661,885 by Milbocker filed Sep. 14, 2000, the teachings of all of these references are incorporated herein. Other attachment mechanisms will also be apparent to those skilled in the art.

In one preferred embodiment, the heart is secured so as to be independent of the skeletal system in the event trauma should occur to the skeletal attachment. Such a trauma would result in impaired heart pumping, even if said trauma would not have otherwise affected the heart. Furthermore, as Heilman et al teach in U.S. Pat. No. 4,925,443, it is necessary to provide for a mechanism to follow the natural movement of the heart, especially torquing forces produced by the contracting heart. In the case of direct attachment to the heart, either through suture or bands placed on the vessels or sinus of the heart, produces localized points of abrasion and force centers which may result in long-term thrombus production or failure of the tissue. One possible acceptable direct attachment to the heart would involve promotion of ingrowth between the heart and wrap. This is a typical condition observed in successful cardiomyoplasty, where the latissimus dorsi bonds to the epicardium. The vacuum attachment method is not preferred since it requires an external vacuum source. Attachment to surrounding tissue is the preferred attachment method of the present invention. These tissues can be used in combination, such as posterior attachments to the pericardium and apical attachment to the diaphragm.

When the wrap is placed around the natural heart and the filling and evacuation of the pumping unit is in phase with the systole and diastole of the natural heart, then the contraction of the wrap around the ventricles of the heart decreases the circumscribed diameter thereby causing the ventricles to eject blood. The wrap operates equally well as a single ventricular assist, however, the wrap ends must be sutured to the septal line of the epicardium. The contractility, and thus the ejection fraction, of the wrap is independent of the number of tubes or the heart dimension. The ejection fraction is only a function of the hydraulic pressure.

Figure 16:
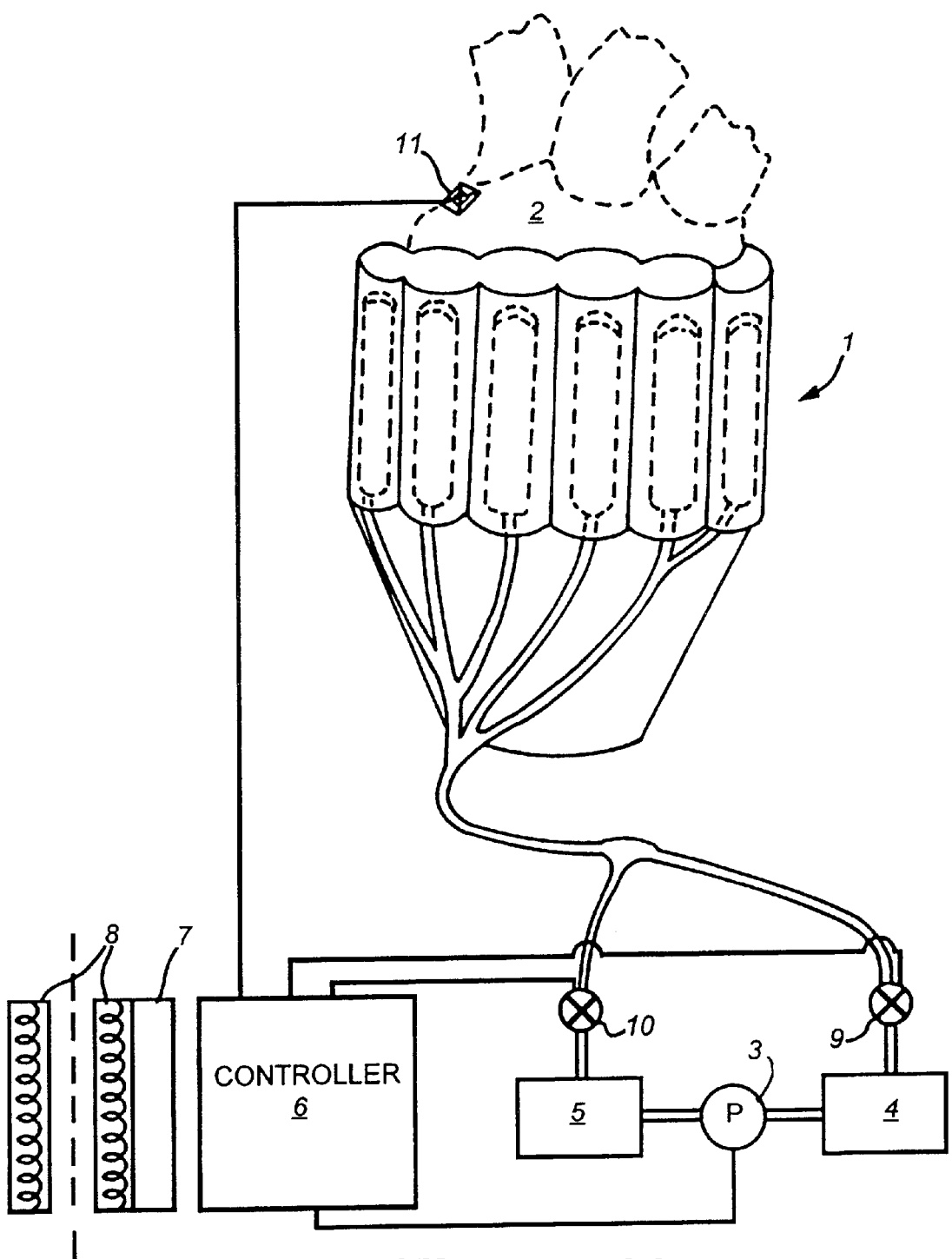
FIG. 16 is schematic diagram of a united system for cardiac assistance according to the invention.

FIG. 16 illustrates a unified system according to the invention implanted in the human body. In the illustrated system the pumping unit 1 is shown as a cuff placed around the ventricles of the natural heart 2. Hydraulic fluid is used to drive the pumping unit, as also taught in U.S. Pat. No. 5,713,954 issued Sep. 3, 1998 entitled "Extra-Cardiac Ventricular Assist Device," herein incorporated by reference. Hydraulic fluid is preferred for the following reasons: 1) a pneumatic system can be susceptible to fluid permeation through the balloons and connecting tubing, whereas the proper choice of a driving fluid substantially eliminates this problem, 2) a gas pressurized system results in a volume expansion in the event of a ruptured line or balloon, whereas a fluid is incompressible, 3) in the event of system failure, the fluid can be drained out of the balloon, and 4) the volume of the pressure and vacuum plenums is smaller. The hydraulic fluid is pressurized by energy converter 3 and fed directly to a spring-loaded hydraulic reservoir 4. The hydraulic reservoir 4 supplies pressurized fluid to the pumping unit 1.

Fluid flows from the pumping unit 1 to a second spring-loaded hydraulic reservoir 5. This reservoir 5 is connected directly to the energy converter 3 to form a closed loop. The energy converter 3, the output of reservoir 4 and the input of reservoir 5 are electrically controlled by virtue of internal electric controller 6 which is powered by an internal battery 7. When the internal electric-controller 6 also supplies the driving energy for the energy converter 3, it is coupled also to external battery 7 via a transcutaneous electrical terminal (TET) 8. For additional details on transcutaneous energy transfer and telemetry, see commonly-owned, co-pending U.S. patent application Ser. No. 09/304,198 filed May 3, 1999 by Kung, the teachings of which are incorporated by reference.

The energy converter 3 may consist of a hydraulic pump coupled to a brushless electric motor to shuttle fluid between reservoir 5 and reservoir 4. This arrangement allows for unidirectional, and continuous operation of the electric motor. Activation of the outlet valve 9 on reservoir 4 and the inlet valve 10 on reservoir 5 is synchronized by a control signal generated by detection of the R wave from the ECG signal collected by electrode 11. Continuous adjustment of the hydraulic pump output allows the level of cardiac assist to be varied on a moving average basis. The duration of the valve opening on reservoir 4 allows the level of assist to be varied on a beat-by-beat basis. Since it is the tendency of the heart to compensate a long beat interval with a short beat interval, this arrangement insulates the motor from erratic variation in beat rate. The motor pump rate will respond to mean pressure variations in the reservoir 4.

Alternatively the energy converter may be a muscle driven unit as taught in U.S. Pat. No. 5,344,385. In this case the muscle used is the latissimus dorsi, and may be stimulated by a low current signal from the electronic controller 6. This approach has the distinct advantage of directly converting mechanical energy to hydraulic energy. The other approach has losses at: 1) the external battery, 2) the TET, 3) the windings in the motor, 4) the conversion of mechanical energy in the motor to hydraulic energy. Typical power consumption for such systems is approximately 20 W. The human heart produces about 1–2 W of hydraulic power. With nearly 100% efficiency between the muscle attachment and the hydraulic compressor mechanism, the power required of the muscle is approximately 2 W. The power available from skeletal muscle has been estimated to be 3 to 15 mW per gram (Geddes et al., (1991), Trans. ASAIO, 37:19–23), a muscle mass of about 116 to 350 grams is generally sufficient within the scope of the present invention. The latissimus dorsi, pectoralis, psoas major, and rectus abdominous muscles are major skeletal muscles capable of supplying sufficient power output. A device as taught in U.S. Pat. No. 5,344,385 makes best use of the muscle by employing the muscle in situ, with a normal pre-stretch, and pulls in tension rather than squeezes, as is the case when the muscle is wrapped around the heart. The time required for contraction is also important. The muscle in the present invention would not be directly coupled to the heart. For beat rates of 70 to 80 beats per minute, the systolic and diastolic intervals are 300 to 500 ms. A stroke length of 4 cm with a contraction time of 300 ms would require an average velocity of 13.3 cm/s. However, 13.3 cm/s is a fast contraction for any skeletal muscle, and is particularly fast for a large muscle. A shorter stroke length results in lower contraction velocities. Thus the optimum design would favor lower contraction velocities and higher exerted forces.

The natural heart pumps blood primarily through circumferential contraction. Most of the diastolic to systolic volume change is derived primarily from the 20% change in the circumference and to a lesser extent to a 9% change in the axial length. The volumetric change in the volume enclosed by the epicardial surface is 36% from the relaxed (diastole) position to the fully contracted (systole) position. As described earlier, for a two-layer geometry the pumping unit generates an 85% ejection fraction. Although a cylindrical geometry was used in the above calculation, when the unit cells are appropriately tapered, the contraction as a percentage of the local heart circumference is the same at all points on the wrap.

With this hydraulic design, the natural heart having a typical myocardium thickness, a heart base diameter of 80 mm and an axial ventricular length from apex to base of 50 mm, a left ventricular wrap results in a stroke volume of 118 ml. This stroke volume exceeds that expected from a normally operating left ventricle. Since the drive pressure rises exponentially near full inflation, normal stroke volumes are achieved at lower inflation pressures.

The pumping unit 1 is activated by a signal from an implanted epicardial lead in a myocardial region of the natural heart not in contact with the pumping unit. Suitable locations are in the apical region or near the right atrial appendage. Release of hydraulic fluid to the wrap is to be timed with the R wave produced on this lead. Detection of the R wave can be accomplished with techniques in use in implantable defibrillators. The systolic duration is preprogrammed (as taught in U.S. Pat. No. 5,713,954 issued Sep. 3, 1998 entitled "Extra-Cardiac Ventricular Assist Device," herein incorporated by reference) to match its functional dependence on the beat rate (BR) in beats per minute expressed as $$t_S = 549 - 2BR. \tag{28}$$

The time delay $t_R$ is the delay between pump initiation relative to the R wave, that is, the interval when the pumping unit is in an evacuated state. The exact coincidence of the start of the diastolic duration and the ECG T-wave is not critical. Irregular rhythms in the natural heart will trigger the system to assume a no pump status. In this state, the pumping unit is evacuated. In the event the ECG signal is lost or too noisy to detect the R-wave, the device could begin contracting at beat rates consistent with maintaining physiological filling pressures. Thus the Unified system would provide the user protection against sudden physiological electrical as well as mechanical failures which may occur in the diseased natural heart.

The control scheme is motivated by the intention to operate the system such that the natural heart maintains a full systolic stroke in every beat. A given hydraulic stroke volume corresponds to an unique contraction; and therefore, there is a one-to-one correspondence between hydraulic stroke volume and physiological stroke volume. If at a given drive pressure the hydraulic stroke volume does not reach the programmed target value, the power required to achieve full stroke can will be automatically adjusted, on a beat by beat basis if necessary. During diastole, the hydraulic pressure will be measured to provide an indication of the end diastolic pressures. From this information a baseline beat rate may be determined, which will automatically be the default operating parameter for the system if the heart should stop beating.

Synchronization is achieved by sensing the natural rhythm of the heart or through implantable pacer electrodes. As is taught in U.S. Pat. No. 5,713,954 issued Sep. 3, 1998 entitled "Extra-Cardiac Ventricular Assist Device," herein incorporated by reference, and is well known in the art, two basic approaches are available. The choice between using the P-wave or the R-wave of the ECG signal is determined by the conduction fitness of the heart.

It is well known that mechanical disruption of the heart can also create electrical changes in the heart. The P-wave may be preferred in this respect since the right atrium is free from mechanical contact with the pumping unit. This approach assumes the right atrium is electrically sound, and free of frequent atrial flutter or fibrillation. Clearly AV block would exclude use of the P-wave. Atrial sensing is accomplished with a lead sutured to the right atrial appendage. Alternatively, in the case of R-wave sensing, a corkscrew electrode is attached to the ventricle near the apex at a location free of wrap contact. In the R-wave sensing mode, it is possible to combine sensing with a means for attaching the pumping unit to the heart. Bipolar electrode designs are known which provide for localized signal reception of the P-wave, providing a reduced noise signal. Unipolar leads are sufficient for R-wave sensing since this is the simplest type of electrode for ventricular epicardial fixation.

Modifications to the control algorithm to accommodate either signal detection method are straight forward and ensure synchronous contraction in the pumping unit. Typically P-wave sensing requires the systolic interval to begin 160 ms after P-wave detection. The systolic interval can be initiated immediately upon detection of the R-wave. U.S. Pat. No. 5,713,954 teaches a possible algorithm based on the prior R-R interval.

U.S. Pat. No. 5,713,954 teaches of a subdermal port for draining the pumping unit in the event of failure of the hydraulic pumping capacity. Such a subdermal port can be accessed through a skin puncture with an array of 15 gauge needles. The procedure would involve extraction of hydraulic fluid using a syringe. The result would be collapse of the wrap. An automated or manually driven pneumatic pump could then be connected to the needle manifold to substitute for the failed hydraulic pumping unit. Pneumatic extracorporeal activation is preferred, since the pressure drop for a hydraulic fluid through the needle array would be unacceptably high.

Implantation of the unified system can require a median stomatomy. An appropriately sized pumping unit would be placed on the natural heart. Laces or adjustable clasps on the V-shaped sections would be used to achieve a closer fit. The hydrogel pocket would be filled as describe earlier to provide a custom fit. The pumping unit would be anchored to the epicardium either by suture or by an adhesive applied between the epicardium and the wrap. The energy converter and the hydraulic reservoirs would be implanted as a unit in the thorax. The energy converter unit would be anchored to the rib cage with a flexible hydraulic connection to the pumping unit and an electrical cable tunneled through the costal diaphragmatic region to the electronic controller that could be implanted in the abdomen. One preferred embodiment of the present invention combines the capacity to run unassisted on the patient's own muscular power as well as allowing assistance through a transcutaneous energy transformer.

With reference again to FIG. 16, a unified system can include the implanted components: a pumping unit, and electronic controller, internal battery, and transcutaneous energy collection and telemetry system. It further includes external components: a transcutaneous energy transmitter and telemetry system, computerized data collection, analysis, and encryption system; and associated batteries, electrical adapters to conventional electrical energy sources, and gear for holding these components.

Figure 17:
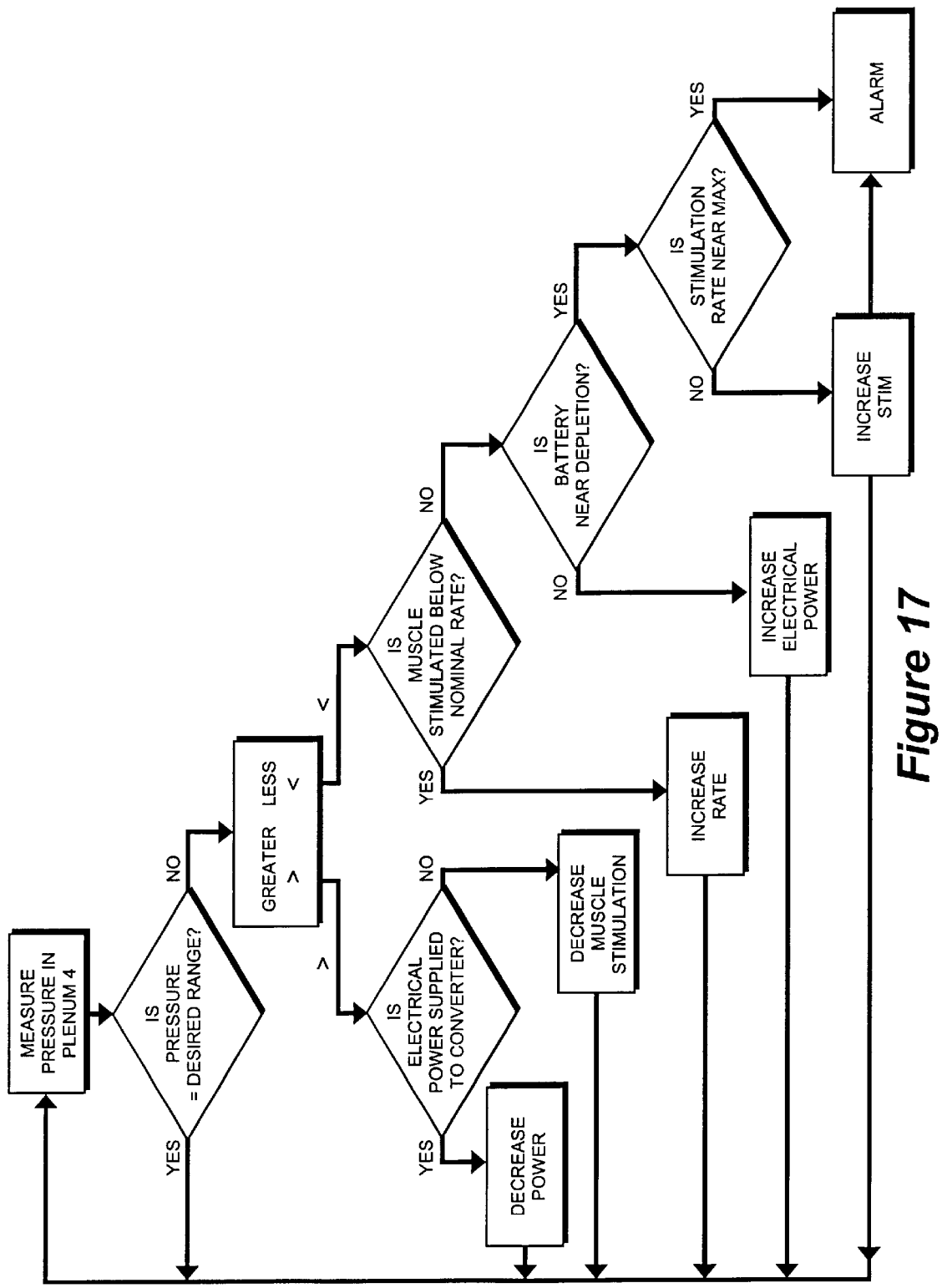
FIG. 17 is a flow diagram of a mode of operation of the invention.

Actuators 9 and 10 converts the actuating signal from the electronic controller 6 into a periodic pressure/volume wavefront in the pumping unit 1. This generates a rhythmic displacement of fluid in the pumping unit, causing a rhythmic fill and drain of fluid in the plenums 5 and 4. The actuating signal is derived from a physiologic ECG signal obtained from an electrode 11 placed on the heart. The energy converter 3 can be an electrical motor powered by the implanted battery 7 or muscle powered or a combination of both. In the case of the muscle powered energy converter, the muscle receives a stimulating signal from the internal electronic controller. This signal can be in response to time varying pumping requirements or to physiologic requirements of the actuating muscle. FIG. 17 provides the decision tree that can be used to govern either mode of operation.

The overall system provides for the optional use of the TET system to power the device. The decision can be sent via the external telemetry to the internal controller, or can be made, as illustrated, predicate on various conditions within the implanted system. In either mode of operation, mean pressures are maintained in the plenums in response to mean pumping demands and desired contraction requirements.

Figure 18:
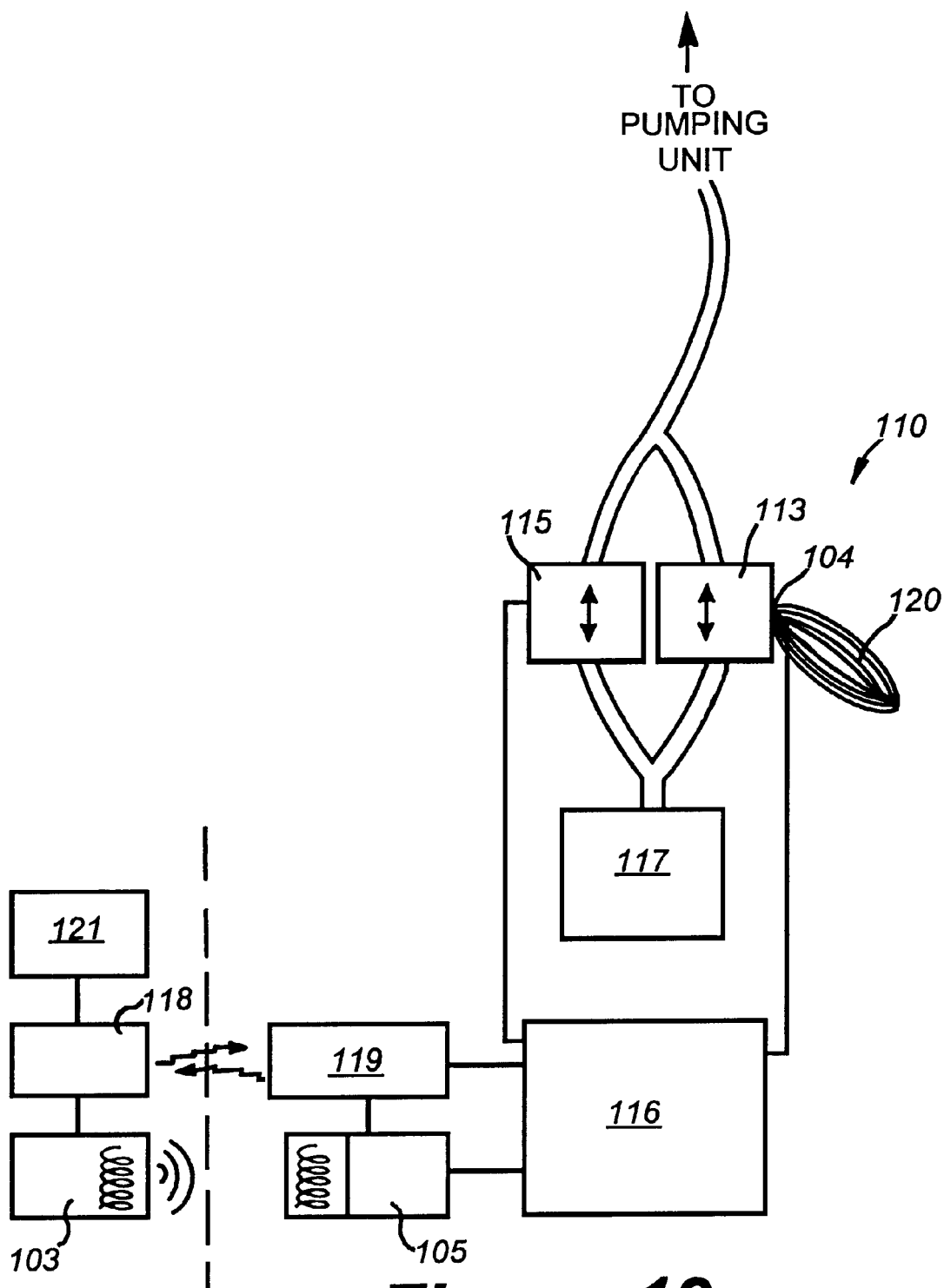
FIG. 18 is a schematic diagram of another embodiment of a cardiac assistance system according to the invention.

The components of a hybrid energy converter are illustrated in FIG. 18 including internal controller 116, internal rechargeable battery 105, internal telemetry transceiver 119, energy converter 110 and plenum 117, as well as external computer 121, external telemetry transceiver 118 and external energy charging source 103. The device is designed to provide a quasi-continuous output.

The internal battery 105 can be connected to the internal controller 116, telemetry transceiver 119, and energy converter 110, via hermetic sealed electrical connectors. The internal battery 105 is preferably implanted subcutaneously in the abdomen. In the preferred embodiment the internal battery package uses rectangular prismatic nickel/cadmium cells, however other battery chemistries could be utilized. These cells are housed in a custom designed laser welded titanium enclosure with a hermetic connector suitable for implantation. The battery housing is arched to provide for good anatomical fit. Preferably the hermetic connector is an internal connector, used for allowing easy replacement of the battery package. In this way, the conductor set need not be changed when and if the internal battery is replaced. The electrical conductor set contains electrical connections for the supply of DC voltage to the internal electronic controller, for the recharging of the internal battery and for activation of -an-audible warning alarm housed in the battery enclosure.

The internal TET/Telemetry unit 105 and 119 can also be implanted subclavicularly. The internal electronic controller 116 receives the transmitted external TET/Telemetry signals from internal TET/Telemetry unit 119. Power signals are passed to a power regulator and telemetry signals to a telemetry subsystem of the internal controller via conductors. A power regulator can generate the DC voltage for supplying the circuits of the internal controller 116 and charging battery 105. The telemetry subsystem exchanges signals with the internal TET/Telemetry unit 9 and with control unit 14. A sensor (as described above) can monitor the pressure in pressure plenum 117 and/or hydraulic fluid consumption. In one embodiment the sensor can be an electrode attached to the heart and monitors the electrical activity of the heart. This allows the electronic controller 116 to provide a Starling type response to physiological changes in oxygen demand. The internal controller 116 processes the data received from the detection means 19 and 16 and instructs the motor commutator 113 or the muscle 120 to generate pressure levels and instructs the inlet/outlet valves to adjust beat frequency, systolic and diastolic duration. Internal controller 116 exchanges information with external computer 121 through telemetry circuit 118.

The transcutaneous energy transformer (TET) and transcutaneous information telemetry (Telemetry) systems can uses wire coils to electromagnetically couple power into the body without perforation of the skin. The Telemetry uses infrared components embedded in the internal and external TET/Telemetry units to transfer the communication channel data streams into and out of the body without EM interference. The external TET/Telemetry system is connected to the external computer via a conductor.

The external computer 121 can contains a portion of the circuitry for TET/Telemetry systems as well as algorithms which can diagnose and specify solutions to emergency situations. In particular the external computer contains detailed specifications for when to deactivate the system so that the pumping unit does not interfere with normal heart function. Additionally, the external computer contains specifications for determining when to operate in a total heart assist mode, usually indicated when abnormal or no electrical signals are received from the heart. It also allows the internal controller to operate in a synchronous and asynchronous mode. The external computer also produces and receives the communication channel data signal for control and monitoring of the implanted system and generates recharging signals for recharging the external battery at predetermined intervals. The external electronics can be a compact unit adapted to be worn on a belt.

Various factors contribute to the fit of an extra-cardiac assist device, among these are: balloon shape (taper), pocket shape, overall shape of the sheath, balloon wall thickness, sheath material stiffness, means for joining the ends of the device, proportion of non-contracting space to contracting space, orientation of the balloons, and size of the balloons. Some design considerations oppose one another. For instance, in the single layer design the circumference of the sheath must be as close as possible to the circumference of the balloon, yet balloon wall thickness and stiffness require the circumference of the sheath to be larger if the balloon is to collapse without wrinkles. Furthermore, overall device flexibility and durability, especially in maintaining tight tolerances, are essential to attaining planned theoretical performance levels.

The considerations listed above are most effective when fitting to heart features of relatively small radius of curvature. For example, it is difficult to fit regions between the right ventricle and the apex. A good fit is possible by inserting a pad between the heart and the device to fill the gap. However, this adds complexity to the design as well as requires a rather precise orientation of the device with respect to the heart. Frequently it is the more subtle features which contribute significantly to device performance. One ideal solution is to form, in situ, a pad between the device and the heart which provides for a custom fit. The pad can be a segmented or a single pocket that extends over the entire inner surface of the device. The pocket can be filled with a hydrogel that forms a layer between the wrap and the heart. The design provides for two entrance ports and an exit port affixed to the pocket. The ports are detachable, and the entrance ports are located at opposite ends of the wrap, the exit port at midway between. A mixture of 10% Hypol and 90% water is mixed in a sealed blender type apparatus. The resultant mixed solution is introduced to the wrap simultaneously through the entrance ports. The pocket is filled until fluid is detected at the exit port, and subsequently the exit port is sealed and the pocket gently pressurized so as to completely fill all voids between the wrap and the beating heart. The solution sets in 60 seconds, allowing for the liquid state of the pocket to be in contact with the beating heart for approximately 30 seconds. The solution sets in a continuous fashion, reaching a maximum durometer reading in about 10 seconds after setting begins. The setting time allows for the pocket to be modified by changes in the heart shape through at least 10 heart cycles, so that the final shape is a fit to the mean heart shape. This provides for the least loading on the device.

The passive system implementation of the present invention can be understood by reference again to FIG. 1A. If the multi-layered balloon elements 304 of the wrap 300 shown in FIG. 1A are filled with a compressible fluid and placed around a patient's heart, the device can both restrain cardiac hypertrophy and mimic the natural resistance of the heart tissue to over-expansion. By choosing an appropriate inflation pressure for the balloon elements 304 and then sealing them, the fluid pressure within the balloons can provide a resistance analogous to the Frank-Starling effect exhibited by cardiac tissue.

In such passive systems, if the heart continues to dilate, the balloons 304 will flatten more to accommodate the enlargement but the pressure applied to the heart by the balloons will be greater. Moreover, unlike mesh-type passive girdles, which rely upon an open structure to accommodate the expansion and contraction of the heart, the multi-layer inflatable structures of present invention permit the use of solid wrap devices, which are less likely to loss their effectiveness over time due to tissue in-growth.

In addition, the passive devices of the present invention can be adjusted. For example, if the heart shrinks, the balloon elements can be periodically filled to a greater extent in order to tighten the wrap and the pressure applied by the partially inflated balloons will be less.

All reference materials cited herein are incorporated by reference.

What is claimed is:

1. An implantable control system for activating a cardiac pumping unit comprising:
    an electronic controller for synchronized release of actuating fluid to a pumping unit and for subsequent synchronized evacuation of fluid from the pumping unit,
    a plenum for storage of a non-pressurized volume of fluid of sufficient size to provide a flow at nearly constant pressure during the release interval, and
    an energy converter for periodically pumping fluid from the storage plenum to the pumping unit and thus attaining a pressurized state in the pumping unit, said energy converter pumping toward the pumping unit during systole and pumping away from the pumping unit during diastole.

2. The control system of claim 1 wherein the system further comprises an electrode for sensing a cardiac electrical signal.

3. The control system of claim 1 wherein the system further comprises:
    a conduit for delivering and distributing a pressurized fluid to the pumping unit,
    an implantable battery and
    a transcutaneous energy receiver for recharging the battery.

4. The system of claim 1, wherein the pumping unit further comprises a collapsible, non-distensible, biocompatible sheath.

5. The system of claim 4, wherein said pumping unit comprises:
    a plurality of elongate inflatable elements each having a longitudinal axis; and
    a sheath defining a set of unit cells, each cell encompassing at least two juxtaposed elongate inflatable members,
    wherein said sheath nondistensibly secures said elongate inflatable elements in a substantially parallel position relative to each other.

6. The system of claim 5, wherein said sheath has a length extending between a first and a second end and a width substantially parallel with said longitudinal axis, said sheath having inner and outer surfaces joined periodically along said length at connection points disposed between said inner and outer surfaces to form a contiguous plurality of unit cells.

7. The system of claim 5, wherein said sheath and said inflatable elements are each constructed of thin, collapsible, non-distensible, and biocompatible material.

8. The system of claim 5, wherein said plurality of inflatable elements and said sheath are integrally formed in a single unit.

9. The system of claim 5, wherein said inflation elements have a top end and a bottom end, and wherein one or more of said top and bottom ends is tapered.

10. The system of claim 5, wherein said first end and said second end of said sheath are connected to form a paraboloid of revolution.

11. The system of claim 5, wherein said plurality of elongate elements are filled with a filler medium to a first amount and wherein the contractile force applied by the pumping unit is proportional to said first amount of a filler medium used to fill said plurality of elongate elements.

12. The system of claim 5, further comprising:
    at least one pocket interposed between the inner surface of the sheath and the heart, the pocket adapted to be filled with a second filler medium at time of implantation to conform said pumping unit to the heart.

13. The system of claim 5, wherein said second filler medium comprises:
    a flexible, deformable substance that substantially maintains its volume when compressed.

14. The system of claim 1, further comprising:
    attachment device configured to prevent said pumping unit from unintentionally adjusting during operation.

15. The control system of claim 1 wherein the system further comprises;
    an internal electronic controller programmed to generate activating signals to control the release of actuating fluid to the pumping unit and for subsequent synchronized evacuation of fluid from the pumping unit, and
    an external controller in radio communication with the internal controller.

16. The implantable cardiac assist system of claim 15 wherein the system further comprises:
    an actuator for converting said actuating signal into a periodic movement of at least one valve member.

17. The implantable cardiac assist system of claim 15 wherein the system further comprises: a volume displacement chamber containing a energy converter and fluid plenums.

18. The implantable cardiac assist system of claim 15 wherein the internal controller further comprises a data transceiver for receiving a data signal from the external controller.

19. The implantable cardiac assist system of claim 15 wherein the internal controller further comprises a data transceiver for transmitting a data signal to the external controller.

20. The implantable cardiac assist system of claim 15 wherein the system further comprises a sensor for sensing electrical signals capable of indicating reliably the cardiac cycle.

* * * * *

UNITED STATES PATENT AND TRADEMARK OFFICE
CERTIFICATE OF CORRECTION

PATENT NO. : 6,540,659 B1
DATED : April 1, 2003
INVENTOR(S) : Michael T. Milblocker It is certified that error appears in the above-identified patent and that said Letters Patent is hereby corrected as shown below:

Title page,
Item [56], References Cited, U.S. PATENT DOCUMENTS, insert missing patent:
-- 5,383,840    1/1995    Heilman et al. --;

Column 14,
Line 30, "FIG 1" should read -- "FIG 1A" --;

Column 22,
Equation 27, "$h_{sigle} = \sqrt{(1-C^2)}\ ^x = 0.37S$" should read -- "$h_{sigle} = \sqrt{(1-C^2)x} = 0.37S$" --;

Column 27,
Line 55, "9" should read -- "119" --;
Line 56, "14" should read -- "104" --;
Line 63, "19 and 16" should read -- "115" --.

Signed and Sealed this

Thirtieth Day of December, 2003

JAMES E. ROGAN
*Director of the United States Patent and Trademark Office*